United States Patent
Omoto et al.

(10) Patent No.: US 7,957,982 B2
(45) Date of Patent: Jun. 7, 2011

(54) DATA MANAGEMENT SYSTEM

(75) Inventors: Masakazu Omoto, Tokyo (JP); Norio Fueki, Tokyo (JP); Koichi Hirose, Orefield, PA (US); Masaya Fujita, Sagamihara (JP); Tetsuyuki Nakahara, Tokyo (JP)

(73) Assignee: Olympus Corporation (JP)

( * ) Notice: Subject to any disclaimer, the term of this patent is extended or adjusted under 35 U.S.C. 154(b) by 1210 days.

(21) Appl. No.: 11/610,147

(22) Filed: Dec. 13, 2006

(65) Prior Publication Data

US 2007/0088753 A1 Apr. 19, 2007

Related U.S. Application Data

(63) Continuation of application No. PCT/JP2005/010722, filed on Jun. 10, 2005.

(30) Foreign Application Priority Data

| Jun. 14, 2004 | (JP) | 2004-176093 |
| Aug. 24, 2004 | (JP) | 2004-243166 |

(51) Int. Cl.
G06Q 10/00 (2006.01)
G06Q 50/00 (2006.01)
(52) U.S. Cl. .......................................................... 705/2
(58) Field of Classification Search ................... 705/2, 3; 345/536
See application file for complete search history.

(56) References Cited

U.S. PATENT DOCUMENTS

2002/0016718 A1\* 2/2002 Rothschild et al. ............... 705/2
2004/0164989 A1\* 8/2004 Utsunomiya et al. ......... 345/536

FOREIGN PATENT DOCUMENTS

| JP | 2001-514775 | | 9/2001 |
| JP | 2001-357242 | A | 12/2001 |
| JP | 2002-63280 | A | 2/2002 |
| JP | 2002-109106 | A | 4/2002 |
| JP | 2002-207822 | A | 7/2002 |
| WO | WO 98/40806 | | 9/1998 |
| WO | WO 02/17171 | A1 | 2/2002 |

OTHER PUBLICATIONS

Japanese Office Action mailed Aug. 18, 2009 in corresponding Japanese Patent Application No. 2004-243166 (in Japanese language).
International Search Report PCT/JP2005/010722 dated Jul. 27, 2005 (Japanese Patent Office).

\* cited by examiner

*Primary Examiner* — Gerald J. O'Connor
*Assistant Examiner* — John A Pauls
(74) *Attorney, Agent, or Firm* — Ostrolenk Faber LLP

(57) ABSTRACT

Mask information for instructing the prohibition of information which cannot be serviced to the outside, is set and inputted by a manager so that the information, the permission of service of which is indicated by the mask information is exclusively sucked up from an in-hospital server by an external server outside the hospital. A service application created for each service reads out and exploits the information needed by itself, from the in-hospital information sucked up by the external server.

6 Claims, 38 Drawing Sheets

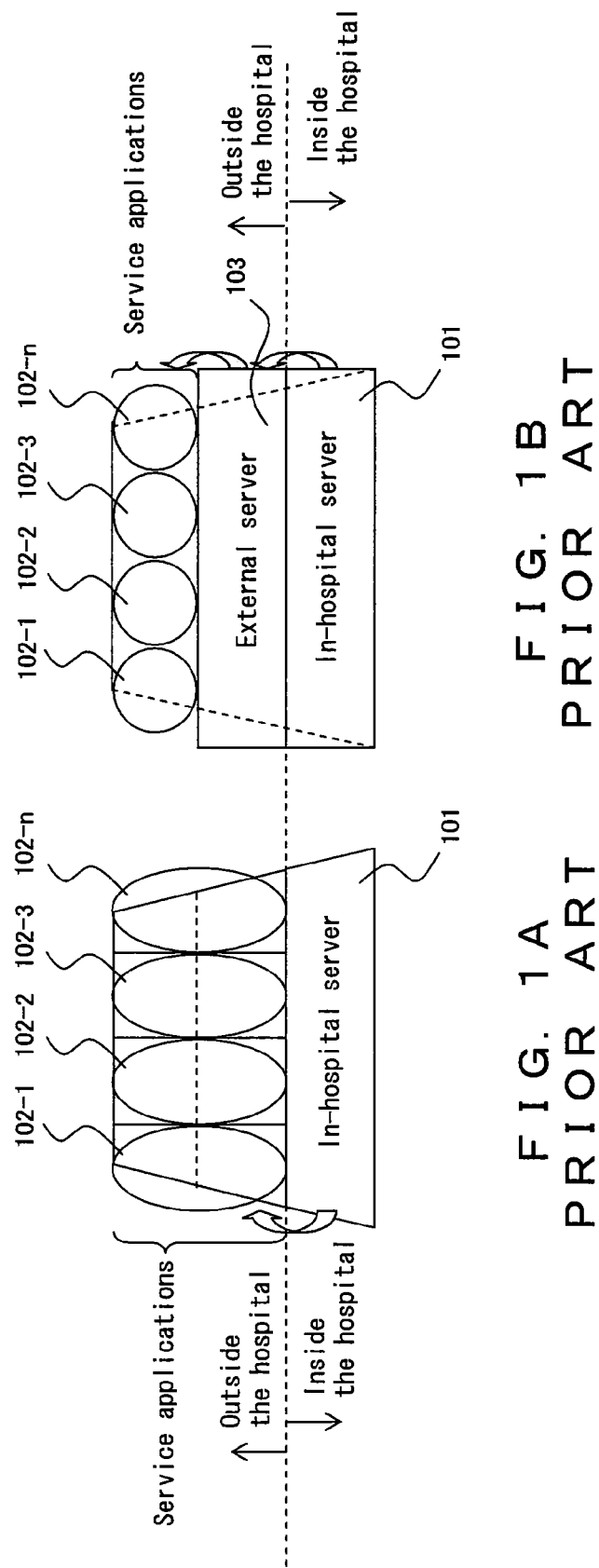

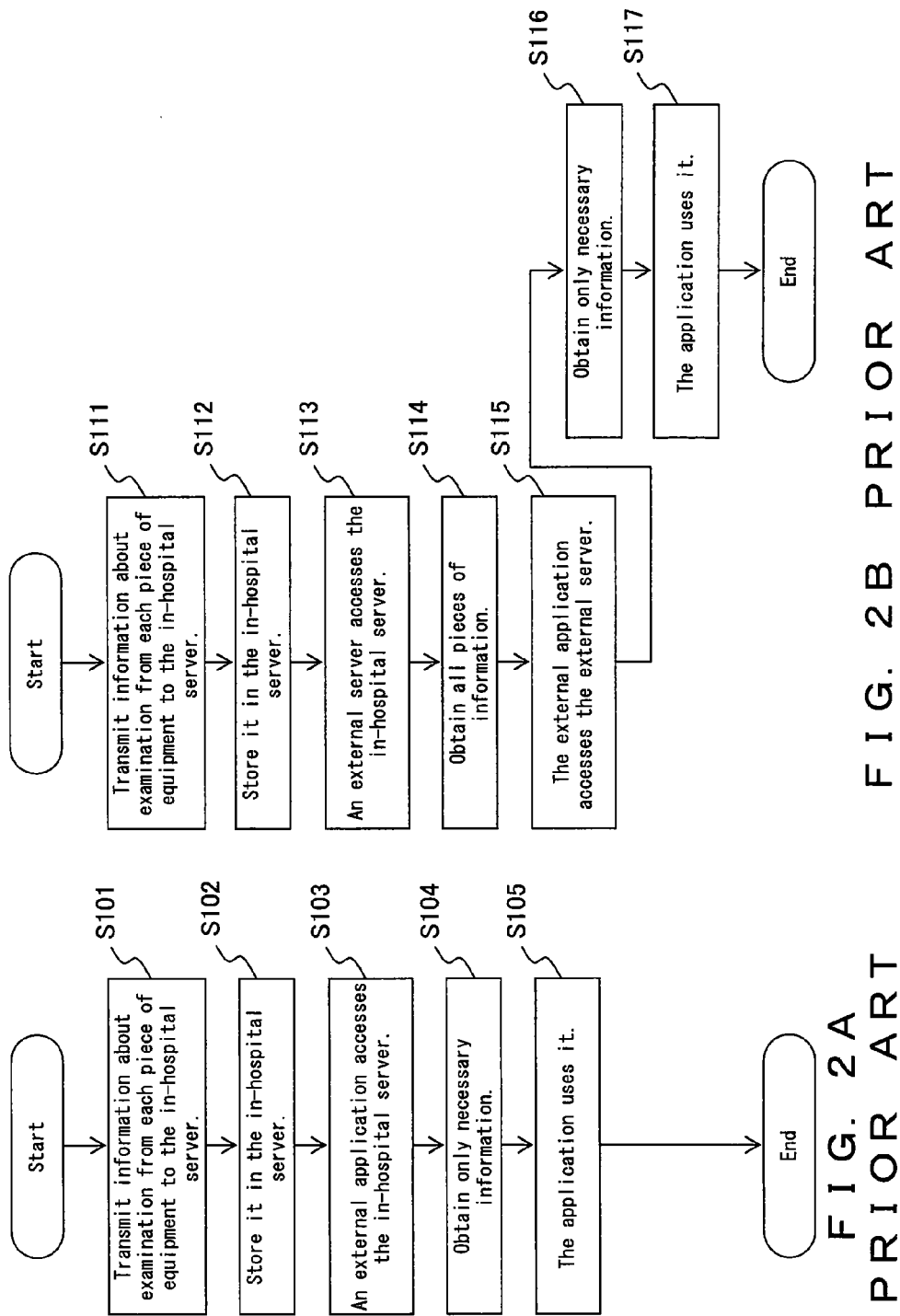

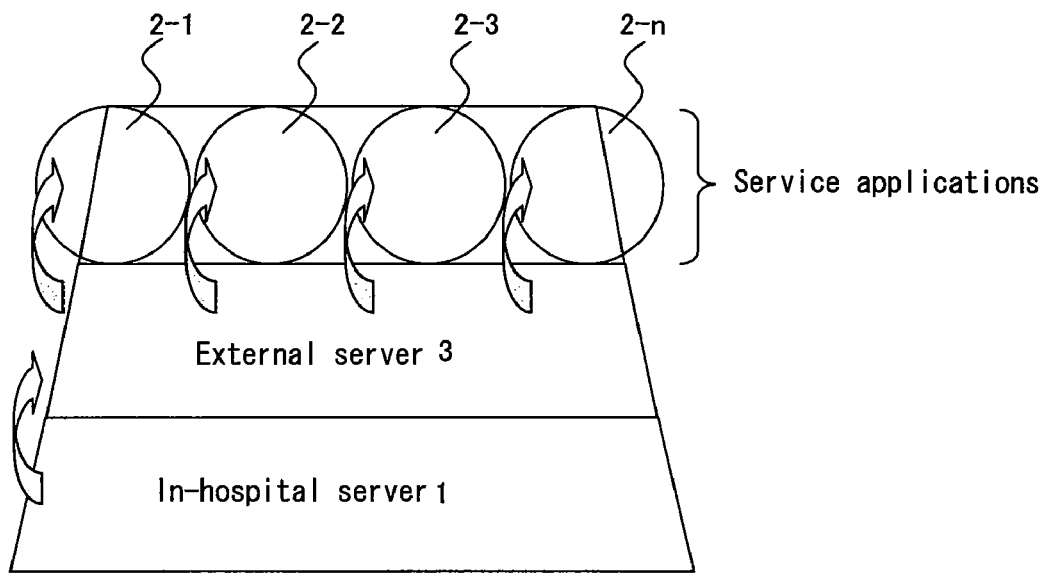
F I G. 3

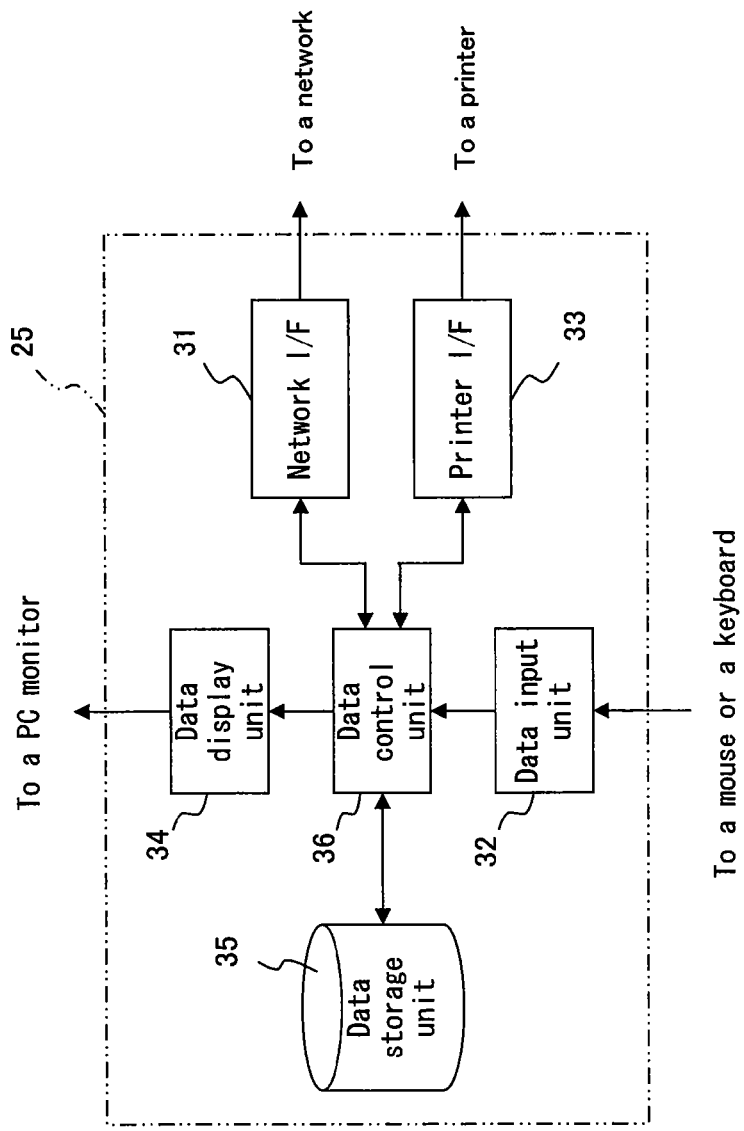
F I G. 6

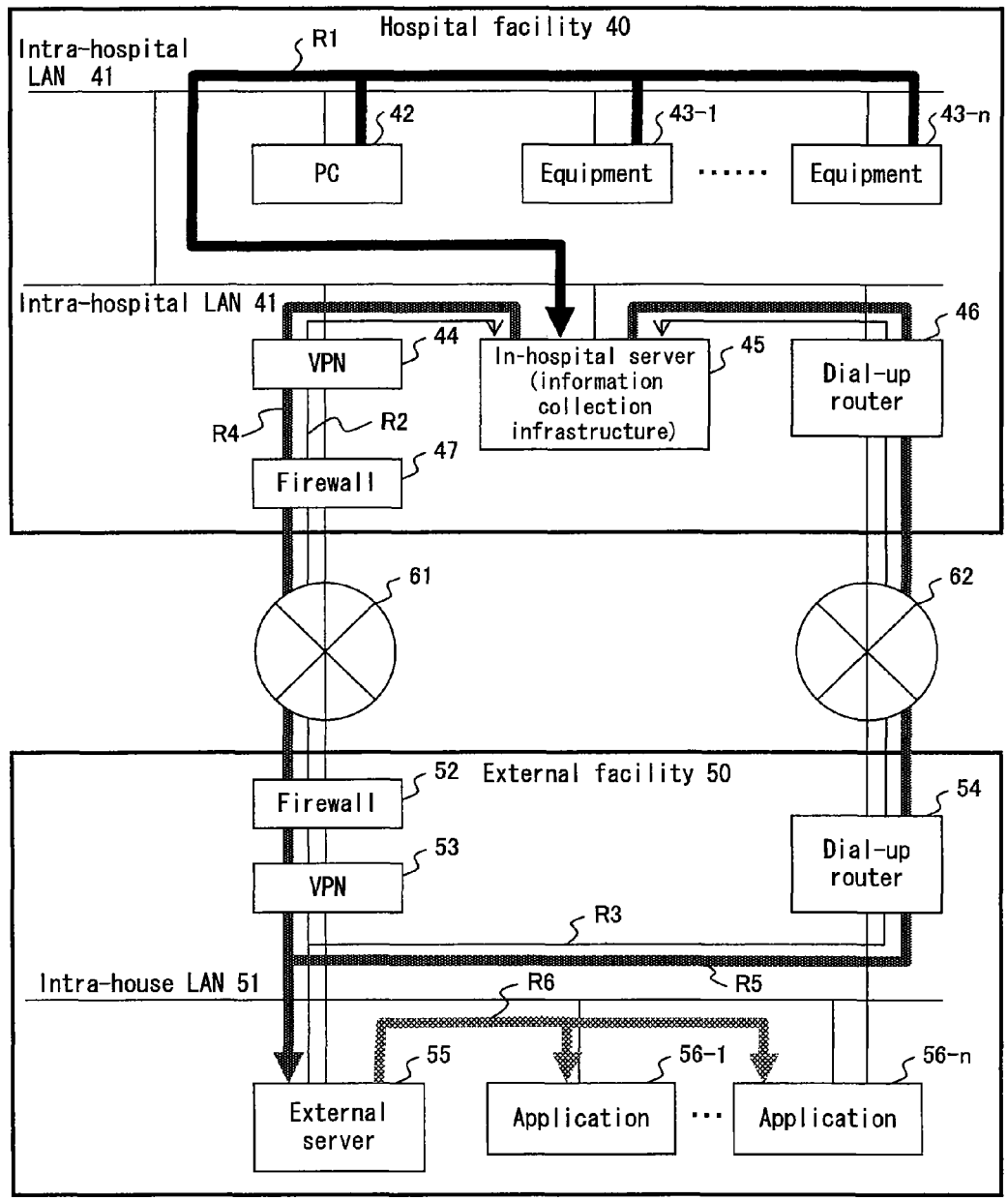
F I G. 7

| Column name | PatientID | PatientName | Age |
|---|---|---|---|
| Japanese name | Patient ID | Patient name | Age |
F I G. 1 1

```
CREATE or REPLACE VIEW ref.patient_table AS SELECT
PatientID,      '------'     as     "PatientName"     Age.....from
act.patient_table;

CREATE or REPLACE VIEW ref.study_table AS SELECT * from
act.study_table;

CREATE or REPLACE VIEW ref.equipment_table AS SELECT *
from act.equipment_table;
```

| Type of upper endoscope | Number of upper endoscopes | Type of lower endoscope | Number of lower endoscopes | Type of video processor | Number of video processors | Type of light source | Number of light sources |
|---|---|---|---|---|---|---|---|
| GIF-160 | 3 | | | CV-165 | 1 | CLV-165 | 2 |
| GIF-180 | 2 | | | CV-160 | 5 | CLV-160 | 3 |

| Type of stocked treatment instrument | Number of stocked treatment instrument | Type of vital sign monitor | Number of vital sign monitors | | Number of endoscopic systems |
|---|---|---|---|---|---|
| Biopsy Forceps | 20 | PV-3002 | 1 | | 1 |
| Retrieval Baskets | 3 | PV-3006 | 2 | | 2 |
| Cyrology Brushes | 14 | | | | |

FIG. 15B

| Name of examined patient | Date of visit | Examination starting time | Type of examination | Used endoscope ID | Name of used endoscope | Number of taken pictures | Report |
|---|---|---|---|---|---|---|---|
| | | 38056 | 0.333333333 | Colon | 1002000 | GIF-190 | 30 | aaaaa |
| | | 38061 | 0.375 | Colon | 1002001 | GIF-190 | 27 | bbbbb |
| | | 38071 | 0.416666667 | Colon | 1002010 | GIF-190S | 28 | ccccc |

| Name of examination doctor | Names of nurses | Name of used treatment instrument | Number of used treatment instrument | Name of used medicine | Amount of used medicine |
|---|---|---|---|---|---|
| John | Nancy | Snear | 2 | Abaivar | 30 |
| Miheil | Hara | | | bbbccefff | 32 |
| Rousher | Rinda | | | Molhiner | 35 |

FIG. 15C

| Facility name | Date of purchase | Unit price | Used frequency | Date of failure | Repair company | Guaranteed period | Available/unavailable | Application date of repair |
|---|---|---|---|---|---|---|---|---|
| HeatProbe | 2002/12/30 | 2,000,000 | 35 | | | 2004/12/31 | Available | |
| Electric | 2003/6/10 | 1,500,000 | 32 | | | 2006/6/9 | Available | |

FIG. 15D

| Name of cleaned endoscope | Cleaned endoscope ID | Date of purchase | Executor name of cleaning | Result of leakage examination | Existence/non-existence of leakage examination | Cleaning executor ID | Cleaning starting time | Cleaning water temperature | Cleaning solution density | Existence/non-existence of air | Existence/non-existence of ??? |
|---|---|---|---|---|---|---|---|---|---|---|---|
| GIF-170 | 4643/5/29 | | James White | OK | Exist | 88812020 | 38071 | 38 | 1900/1/10 | Not exist | Not exist |
| GIF-180 | 3421/12/29 | | James White | OK | Exist | 88812020 | 38071 | 38 | 1900/1/10 | Exist | Not exist |
| GIF-Q180 | 5240/3/29 | | James White | NG | Exist | 88812020 | 38071 | 38 | 1900/1/10 | Exist | Exist |

| Existence/non-existence of water supply pipe cleaning | Error occurring time | Error cause | Power on time |
|---|---|---|---|
| Not exist | Not exist | | 0.375 |
| Not exist | Not exist | | 0.375 |
| Exist | 0.570833333 | Water leakage | 0.375 |

FIG. 15E

| Number of endoscopic doctors | Number of nurses | Number of cleaners | Number of cleaning per day | Total number of VSMs | Total number of endoscopes | Total number of video processors | Total number of light sources |
|---|---|---|---|---|---|---|---|
| 4 | 7 | 2 | 21 | 7 | 7 | 7 | 4 |

208

| Field information | Mask information |
|---|---|
| Patient name | Exist |
| Weight | Exist |
| Examination doctor | Not exist |
| Type of examination | Not exist |
| Date of examination | Not exist |
| ... | ... |

501 — Field information column
502 — Mask information column
500-1, 500-2, 500-3, 500-4, 500-5 — row labels

| Field information | Mask information |
|---|---|
| Patient name | Exist |
| Weight | Exist |
| Examination doctor | Exist |
| Type of examination | Not exist |
| Date of examination | Not exist |
| ... | ... |

501 — Field information column
502 — Mask information column
500-1, 500-2, 500-3, 500-4, 500-5 — row labels

FIG. 23

|  | 900 | | |
|---|---|---|---|
| Field information (902) | Examination 1 (903-1) | Examination 2 (903-2) | ... |
| Patient name (901-1) | × | × | ... |
| Weight (901-2) | × | × | ... |
| Examination doctor (901-3) | ○ | ○ | ... |
| Type of examination (901-4) | ○ | ○ | ... |
| Date of examination (901-5) | ○ | ○ | ... |
| ... | ... | ... | ... |

FIG. 25

| Field information | Old mask table mask information | New mask table mask information |
|---|---|---|
| Patient name | Exist | Exist |
| Weight | Exist | Exist |
| Examination doctor | Not exist | Exist |
| Type of examination | Not exist | Not exist |
| Date of examination | Not exist | Not exist |
| ... | ... | ... |

F I G. 2 7

900

| Field information | Examination 1 | Examination 2 | Examination 3 | ... |
|---|---|---|---|---|
| Patient name | × | × | × | ... |
| Weight | × | × | × | ... |
| Examination doctor | ○→× | ○→× | × | ... |
| Type of examination | ○ | ○ | ○ | ... |
| Date of examination | ○ | ○ | ○ | ... |
| ... | ... | ... | ... | ... |

| | Field information | Old mask table mask information | New mask table mask information |
|---|---|---|---|
| 1401-1 | Patient name | Exist | Exist |
| 1401-2 | Weight | Exist | Not exist |
| 1401-3 | Examination doctor | Not exist | Not exist |
| 1401-4 | Type of examination | Not exist | Not exist |
| 1401-5 | Date of examination | Not exist | Not exist |
| | ... | ... | ... |

1402, 1403, 1404

F I G. 3 0

|  | contents of examination | Weight |
|---|---|---|
| 1501-1 | Examination 1 | 68 |
| 1501-2 | Examination 2 | 49 |
| 1501-3 | Examination 3 | 72 |
|  | ... | ... |

FIG. 31

|  | Field information | Examination 1 | Examination 2 | Examination 3 | ... |
|---|---|---|---|---|---|
| 901-1 | Patient name | × | × | × | ... |
| 901-2 | Weight | ×→○ | ×→○ | ○ | ... |
| 901-3 | Examination doctor | ○ | ○ | ○ | ... |
| 901-4 | Type of examination | ○ | ○ | ○ | ... |
| 901-5 | Date of examination | ○ | ○ | ○ | ... |
|  | ... | ... | ... | ... | ... |

F I G. 3 2

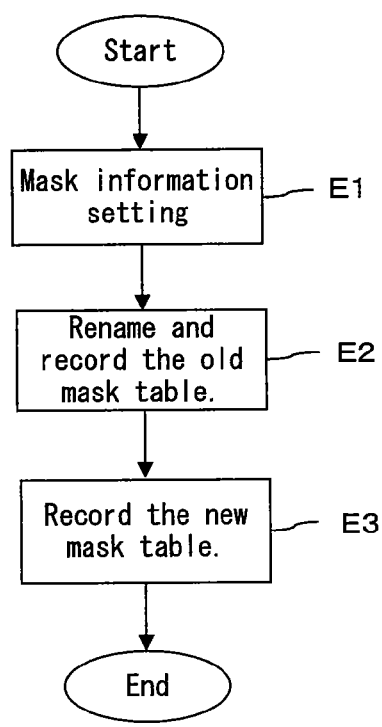
F I G. 3 4

DATA MANAGEMENT SYSTEM

CROSS REFERENCE TO RELATED APPLICATIONS

This application claims benefit of Japanese Application No. 2004-243166 filed Aug. 24, 2004, the contents of which are incorporated by this reference.

This application is a continuation of PCT application No. PCT/JP2005/010722, which was filed on Jun. 10, 2005.

BACKGROUND OF THE INVENTION

1. Field of the Invention

The present invention relates to a system for managing electronic data handled inside a hospital, and more particularly relates to how to transfer electronic data when transferring the data to outside the hospital.

2. Description of the Related Art

Currently in a medical field too, with the development of a network technology and an information processing technology, a system for digitalizing information used inside a hospital facility, such as information about various types of medical actions, accounting information and the like, and exchanging this via a network is devised and put into practical use.

For example, Patent reference 1 (Japanese Patent Application No. 2002-207822 (FIG. 1, paragraphs [0010]~[0014]) discloses a system for exchanging medical information and the like by connecting an area information server provided for each area to a general home and a terminal provided for a medical facility in that area via a network or connecting each area information server and a comprehensive information server for exchanging data via a network, such as the Internet or the like.

Inside a hospital, with the advance of medical information connection system, such as a hospital information system (HIS) and the like, various data of a patient and its medical actions transmitted from examination equipment or a terminal device via a network is stored in/managed by an in-hospital server provided for each hospital.

It is considered that various types of information stored in/managed by the server in this hospital is used not only inside the hospital but also secondarily used outside the hospital. However, in this case, the rare data stored in the database of the in-hospital server is transferred to outside the hospital by copying it to a server outside the hospital. Alternatively, a service application outside the hospital directly obtains data field s to be secondarily used from the in-hospital server and uses them.

FIG. 1 shows how to conventionally transfer data to outside the hospital.

In FIG. 1A, each service application 102 for providing services using data stored in an in-hospital server 101 subsequently reads data from the in-hospital server individually. In FIG. 1B, an external server collectively sucks up data stored in the in-hospital server.

In the case of FIG. 1A, each of service applications 102-1~102-n individually accesses the in-hospital server 101 via a network and reads out necessary data.

In the case of FIG. 1B, an external server 103 sucks up all pieces of data stored in the in-hospital server 101 via a network and each of the service applications 102-1~102-n reads out necessary data from this external server 103 and secondarily uses it.

FIG. 2 is a flowchart showing the process of transfer data as shown in FIG. 1A.

FIG. 2A shows the process shown in FIG. 1A. In FIG. 2A when the process is started, firstly in step S101, information about examination is transmitted from each piece of examination equipment in the hospital to the in-hospital server 101. Then, in step S102, the in-hospital server 101 registers and stores this information in an internal database.

In this state, in step S103, each service application 102 for secondarily using data in the in-hospital server 101 accesses the in-hospital server 101 via a network to obtain only necessary information from the in-hospital server 101 (step S104). Then, each service application 102 uses this information to realize services (step S105).

FIG. 2B shows the process shown in FIG. 1B. In FIG. 2B when the process is started, as in FIG. 2A, firstly in step S111, information about examination is transmitted from each piece of examination equipment to the in-hospital server 101. Then, in step S112, the in-hospital server 101 registers and stores this information in an internal database as in-hospital information.

In this state, in step S113, the external server 103 accesses the in-hospital server 101 via the network to suck up and obtain all pieces of in-hospital information stored in the database and stored/accumulated in the in-hospital server 101.

Then, in step S113, each service application 102 for secondarily using data in the in-hospital server 101 accesses the external server 103 via the network to obtain only necessary in-hospital information from the external server 103 (step S114). Then, each service application 102 uses this information to realize services (step S115).

As described above, when using in-hospital information outside the hospital, conventionally each service application 102 directly obtains and uses information collected in the in-hospital server 101 (method 1). Alternatively, the external server 103 sucks up all pieces of information in the in-hospital server 101 and service application 102 uses only necessary (method 2).

In method 1, since necessary information can be obtained on demand by an out-hospital server accessing an in-hospital server, necessary information can be obtained and processed for each service application. However, in this case, the more the number of service applications becomes, the more the number of accesses to the in-hospital server becomes. Therefore, it becomes more difficult to protect security and load to the in-hospital server becomes larger. Furthermore, when a plurality of service application must be generated, a mechanism for obtaining information from the in-hospital server must be provided for each service application and the in-hospital server. Therefore, it takes much time and labor to extend the entire system including the in-hospital server, out-hospital server or service applications. In method 2, since all pieces of information in the in-hospital server is sucked up, information which a hospital does not want to go out of the hospital and information which a law/regulation prohibits from going out of the hospital is also sucked up. Furthermore, since all pieces of information in the in-hospital server are sucked up, the transfer amount of data increases to give a large load to the out-hospital and in-hospital servers.

Patent reference 1: Japanese Patent Application No. 2002-207822 (FIG. 1, paragraphs [0010]~[0014])

Patent reference 2: Re-published WO02/017171 (pages 14~25, FIGS. 1~9)

SUMMARY OF THE INVENTION

Therefore, it is an object of the present invention to provide a data management system with a mechanism for efficiently sucking up necessary information from an in-hospital server in order to provide each service.

It is another object of the present invention to provide a data management system for efficiently sucking up necessary information from an in-hospital server in order to provide each service while preventing information which a hospital does not want to go out of the hospital from the in-hospital server, such as personal information and the like, or information which a law/regulation prohibits from going out of the hospital, from leaking from the in-hospital server.

Furthermore, it is another object of the present invention to provide a highly extendable data management system capable of minimizing the number of modification points even when the number of services increases to increase the number of service applications for providing the services.

An in-hospital information processing device for storing and managing in-hospital information handled in a hospital comprises an in-hospital information storage means (or in-hospital information storage unit), a mask means (or mask setting unit) and a publishable information generation means (or publishable information generation unit) in order to solve the above-described problems.

The in-hospital information storage means stores and accumulates in-hospital information collected from within the hospital.

The mask setting means sets mask information indicating whether the in-hospital information stored in the in-hospital information storage means should be permitted to provide to outside the hospital.

The publishable information generation means generates only publishable information which is permitted to provide or output to outside the hospital via a communication line, based on the mask information.

An out-hospital information processing device installed outside a hospital comprises a publishable information reading means (or publishable information reading unit) and a publishable information storage means (or publishable information storage unit).

The publishable information reading means reads out the publishable information from the in-hospital server.

The publishable information storage means stores the publishable information read out from the in-hospital server.

By adopting such configurations, an external server can read out only publishable information excluding in-hospital information whose provision to outside the hospital is prohibited. Therefore, in-hospital information whose provision to outside the hospital is prohibited can be prevented from being read by an external server.

BRIEF DESCRIPTION OF THE DRAWINGS

FIG. 1A shows how to conventionally transfer data to outside a hospital (No. 1);
FIG. 1B shows how to conventionally transfer data to outside a hospital (No. 2);
FIG. 2A is a flowchart showing the conventional process of transferring data (No. 1);
FIG. 2B is a flowchart showing the conventional process of transferring data (No. 2);
FIG. 3 shows how to transfer in-hospital information to outside the hospital in the data management system of the preferred embodiment;
FIG. 6 shows the configuration of the in-hospital server;
FIG. 7 shows the basic configuration of the entire data management system in the preferred embodiment and its flow of information;
FIG. 11 shows an example of in-hospital information stored in the in-hospital server;
FIG. 12 shows an example of a definition sentence by a SQL code, for generating publishable in-hospital information View;
FIG. 15A shows an example of publishable in-hospital information sucked up from a hospital by an external server;
FIG. 15B shows another example of publishable in-hospital information sucked up from a hospital by the external server (No. 1);
FIG. 15C shows another example of publishable in-hospital information sucked up from a hospital by an external server (No. 2);
FIG. 15D shows another example of publishable in-hospital information sucked up from a hospital by an external server (No. 3);
FIG. 15E shows another example of publishable in-hospital information sucked up from a hospital by an external server (No. 4);
FIG. 21 shows an example of a mask table recorded on the terminal;
FIG. 23 shows an example of a mask table whose mask information is already modified;
FIG. 25 shows an example of a database provided for a database management terminal;
FIG. 27 shows an example of the mask table in the case where old and new mask tables are combined;
FIG. 28 shows the database in the case where all examination contents areas corresponding to the modified mask information is nullified.

FIG. 30 shows an example of the mask table obtained by combining old and new mask tables;

FIG. 31 shows the data table of in-hospital information extracted from the database of an information storage server;

FIG. 32 shows how to additionally record lacking in-hospital information on the database;

FIG. 34 is a flowchart showing the operation of a terminal;

DESCRIPTION OF THE PREFERRED EMBODIMENTS

One preferred embodiment of the present invention is described below with reference to the drawings.

FIG. 3 shows how to transfer in-hospital information to outside the hospital in the data management system of this preferred embodiment.

In this preferred embodiment, various types of information is collected from each diagnosis and treatment department and a reception in a hospital via an intra-hospital LAN installed in the hospital, and is stored in the database and stored in an in-hospital server (also called "in-hospital information processing device") 1. Then, the manager sets and inputs mask information for instructing the provision prohibition of information whose provision to outside the hospital is prohibited, such as information to be related to the privacy of a patient, of the various types of collected information. Then, information which is permitted to provide is generated based on this mask information, and an external server (also called "out-hospital information processing device") 3 located outside the hospital sucks up only the information via a communication line (for example, a public network, such as the Internet or the like). Then, each of service applications 2-1~2-n generated for each service provides services by reading out its necessary information from the in-hospital information stored in the external server 3, whose provision to outside the hospital is permitted, and using it.

Thus, information whose provision to outside the hospital is not desired, such as the personal information of patients and the like can be preventing from externally leaking. Since each of the service applications 2-1~2-n reads out necessary information not from the in-hospital server but from the external server 2, the restriction of data transfer speed is loose. Furthermore, when a new external service application 2 must be generated, by extracting in advance information excluding one whose provision to outside the hospital is prohibited, from the data of the in-hospital server 1 to the external server 3 and a service application 2 for secondarily using the data using it, redundancy can be eliminated and extensibility can be provided.

In this specification, a term "in-hospital server" includes all servers for collecting, storing and managing electronic data inside a hospital, such as a server for storing and managing information handled inside the entire hospital facility, a server provided for each diagnosis and treatment department and other departments of the hospital and the like.

Figure 4:
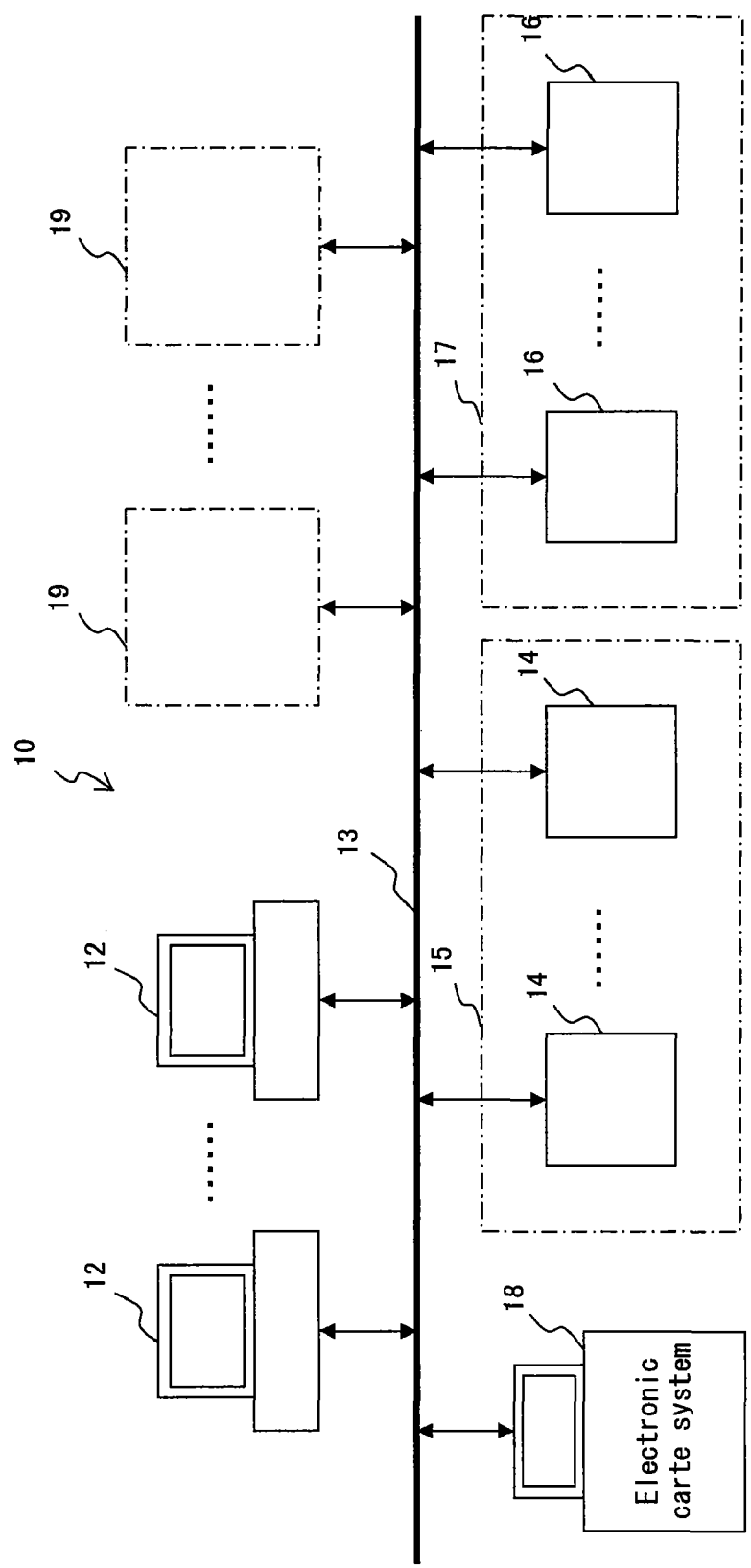
FIG. 4 shows the basic configuration of all components installed inside the hospital, of the data management system in the preferred embodiment.

FIG. 4 shows the basic configuration of all components installed inside the hospital, of the data management system in the preferred embodiment.

In a data management system (also called "in-hospital system") 10, a plurality of terminals 12, 14 and 16 are connected to each other by a LAN 13.

The terminal 12 is used to refer to data stored in the data management system 10. In FIG. 4, portions enclosed by dotted lines 15, 17 and 19 indicate department systems provided for each diagnosis and treatment department in a hospital, and the terminals 14 and 16 indicate ones belonging to each diagnosis and treatment department. For example, in a diagnosis and treatment department 15, when inspecting using an endoscope, the terminal 14 is used to prepare an examination report by displaying the sensed image of the endoscope, inputting the opinion of a doctor, and so on. In a diagnosis and treatment department 17, the terminal 16 is provided to prepare an examination report by displaying an image obtained in an examination and inputting the opinion of a doctor. The terminals 14 and 16 can also be medical equipment connected to a network.

Figure 5:
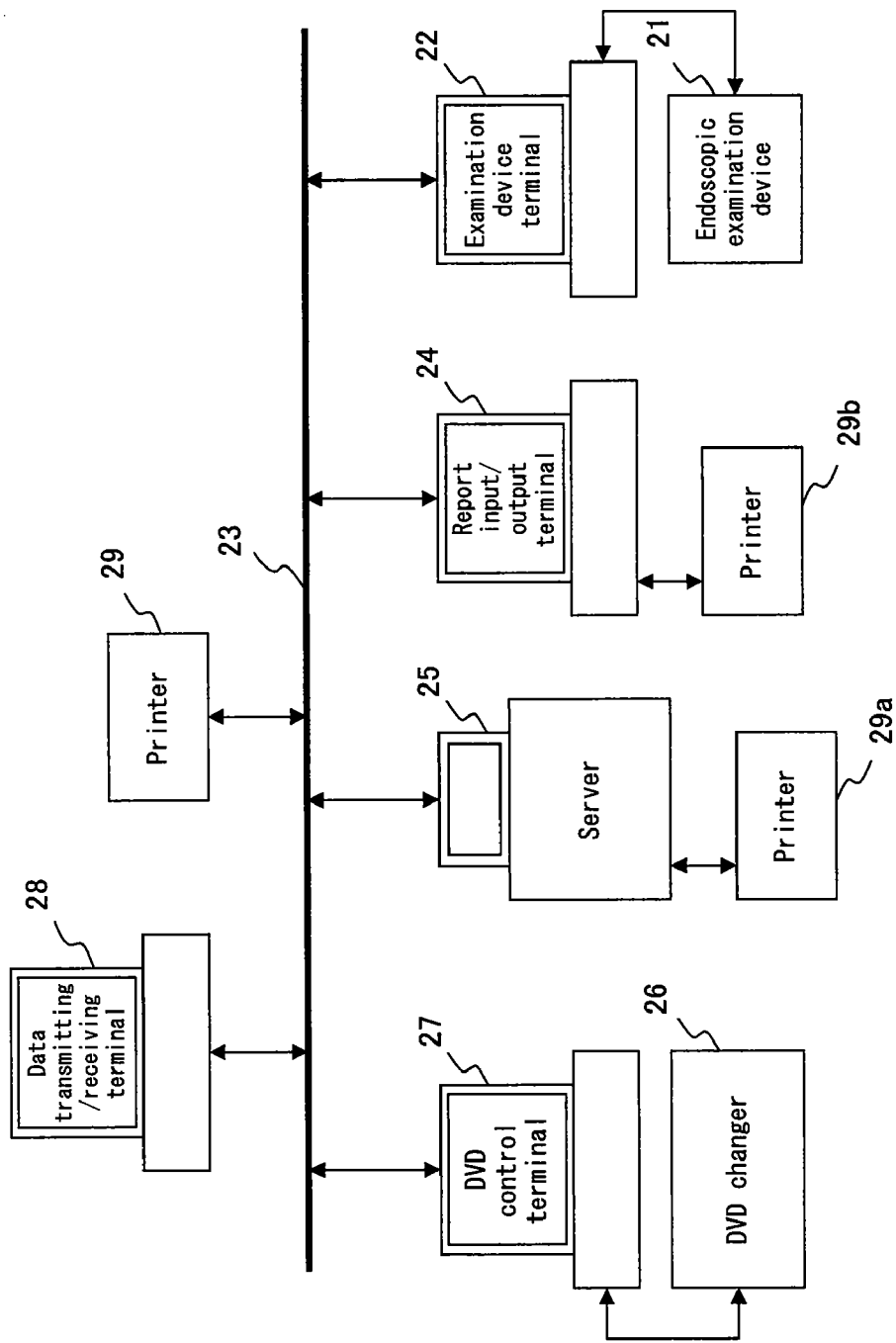
FIG. 5 shows the configuration of a system provided for a diagnosis and treatment department.

FIG. 5 shows the configuration of a system provided for a diagnosis and treatment department. FIG. 5 corresponds to the diagnosis and treatment department 15 shown in FIG. 4.

In FIG. 5, to a LAN 23, which is a part of the LAN 13 shown in FIG. 4, an examination device terminal 22, a report input/output terminal 24, a data transmitting/receiving terminal 28 and a printer 29 are connected, and data can be exchanged among them via the LAN 23.

The examination device terminal 22 is an information processing terminal for controlling an examination instrument and processing data, such as an examination result and the like. In FIG. 5, an endoscopic examination device 21 is shown as an example of the examination instrument handled by the examination device terminal 22. The image data of an image sensed by the endoscopic examination device 21 is taken into the examination device terminal 22. The examination device terminal 22 also specifies the type of the endoscopic examination device 21 and so on.

The report input/output terminal 24 is used for a doctor conducting an examination to prepare a report by input its opinion and so on. A report prepared on this report input/output terminal 24 is transmitted to an in-hospital server 25 and a DVD control terminal 27. The report prepared by the report input/output terminal 24 can be printed by the printer 29b connected to this.

The in-hospital server 25 classifies data, such as patient information, including the name and age, of a patient, examination information, including image data obtained by an examination and a report describing the opinion of a doctor, equipment information, including the type and used time of a used examination instrument, user information, which is information about hospital staff, including a doctor and a nurse and the like, and stored the data in the database. These pieces of information collected via the LAN 23 are stored in the database as in-hospital information and is stored. The in-hospital server 25 also prints the information using the printer 29a, based on a user's instruction. The DVD control terminal 27 stores image data obtained by an examination in a DVD mounted on a DVD changer 26 and reads out image data stored in the DVD.

The data transmitting/receiving terminal 28 receives the data of a patient from an electronic carte system 18 and accesses the data of another diagnosis and treatment department. The printer 29 is generally used to print data received by the data transmitting/receiving terminal 28 and to print data for a general purpose.

FIG. 6 shows the configuration of the in-hospital server 25 shown in FIG. 5.

For the in-hospital server 25, an ordinary general-purpose computer can be used. For example, its configuration is as shown in FIG. 6.

In the configuration shown in FIG. 6, a data control unit 36, which can be realized by a CPU or the like, processes data, based on a program stored in a data storage unit, and realizes a process described later by storing data in the data storage unit 35 as requested and reading out data from the data storage unit 35. To a data input unit 32, an input device for a user inputting an instruction, such as a pointing device, including a mouse, a keyboard or the like is connected. By operating this input device, a doctor inputs information, such bas its opinion and the like. A data display unit 34 is connected to a PC monitor and transmits data for displaying an information setting/input screen, which is described later, on the PC monitor, to the PC monitor. A network I/F 31 is an interface for exchanging data with another device via the intra-hospital LAN. To a printer I/F 33, a printer is connected, and prints and outputs in-hospital information stored in an external server and the like.

FIG. 7 shows the basic configuration of the entire data management system in the preferred embodiment and its flow of information.

In FIG. 7, a service center for providing the management service of equipment used for examination, using in-hospital information handled in a hospital sucks up in-hospital information composed of character data, image data and the like, from the hospital, and provides services, such as the maintenance management of an examination instrument, charging and the like, using this in-hospital information.

A variety of information generated in equipment 43-1~43-m, such as an examination instrument, its terminals (corresponding to the endoscopic examination device 21 and examination device terminal 22 shown in FIG. 5) and one or a plurality of terminal devices 42 (corresponding to the terminals 12, 14 and 16 shown in FIG. 4), which are connected to an intra-hospital LAN 41, which is a network inside a hospital facility 40 is transmitted to an in-hospital server 45 (corresponding to the in-hospital server 25 shown in FIG. 5) via the intra-hospital LAN 41 (corresponding to the LAN 13 shown in FIG. 4) as shown by a route R1 and is stored/accumulated in the in-hospital server 45.

When the read request of data stored in the in-hospital server 45 is issued from an external server 55 in an external facility 50, such as a service center located outside the hospital facility 40, to the in-hospital 45 via a route R2 (or R3), only information whose provision to outside the hospital the hospital side permits is sucked up by and stored in the external server 55 via a route R4 (or R5), which is the route the reversal of the route R2 (or R3).

The information stored in the external server 55 is obtained by service applications 56-1~56-n via an intra-house LAN 51 as shown in a route R6, upon the request of a service application used for each service, and is secondarily used in various ways.

On the route R2 (or R4) of the information routes shown in FIG. 7, information is exchanged via a network 61 of the Internet. On the route R2, the external server 55 in the external facility 50 and the in-hospital server 45 in the hospital facility 40 are connected to the network 61 via a virtual private network (VPN) 44 (VPN 53) and a firewall 47 (firewall 52) to improve the security of data communication. On the route R3 (and R5), information is exchanged via a network 62 using a public line, such as a telephone line or the like. On the route R3 (and R5), the external server 55 in the external facility 50 and the in-hospital server 45 in the hospital facility 40 are connected to each other via the network 62, using a dial-up router 46 (dial-up router 54).

Although in FIG. 7, the external facility 50, being a service center, is connected to one hospital facility 40, the external facility 50 can also be connected to a plurality of hospital facilities 40 via the networks 61 and 62, and can provide services by sucking up in-hospital information from the plurality of these hospital facilities 40. In this case, by targeting a plurality of hospitals, wider services can be provided using in-hospital information collected from the plurality of hospitals.

Although service applications 56-1~56-n are provided in the same external facility 50 as the external server 55, a part or all of these service applications 56-1~56-n can also be provided in a facility different the external facility 50 in which the external server 55 is installed and necessary in-hospital information can be read from the external server 55 via a dedicated line or the networks 61 and 62.

In such a system configuration, for example, in the case of an endoscopic examination, an endoscopic examination device for conducting an endoscopic examination transmits equipment use information, examination information, examination result information, sensed image information and the like from the endoscopic examination device terminal 43 to the in-hospital server. When cleaning an endoscope after examination, cleaning information is transmitted from an endoscope cleaning device to the in-hospital server.

The in-hospital server 45 records and manages equipment/facility information, such as the number of endoscopic examination rooms, the number of endoscopic examination devices, the number of endoscopes, the number of endoscope cleaning devices as in-hospital information in addition to information about patients and examination transmitted from each piece of equipment 43 and each terminal from time to time. Then, by the mask setting process described later, the manager of the in-hospital server inputs mask information indicating whether the provision to outside the hospital of the information should be permitted, and the external server 55 sucks up only information whose provision to outside the hospital is permitted according to this mask information. In this case, such information can also be outputted to the external server 55.

Then, in the external facility, the service application 56 realizes services using the information sucked up by the external server 55.

As such services, a consultant service of calculating by how many endoscopes and endoscope cleaning machines an examination can be efficiently conducted in this hospital, based on the number of endoscopic examinations, an examination time, the number of doctors and nurses, the number of examination rooms, the number of endoscopes, the number of endoscope cleaning machines, etc., of information stored in the external server 55, giving advices about the efficient use of equipment and giving consultations on the installation/introduction of endoscopic examination related facilities when installing a new hospital and when introducing such facilities, an equipment lease charging service of charging for the use of the device, based on the number of endoscopic examinations, the use of a special function of the endoscopic device, the used frequency of an endoscope, etc., and the like can be considered.

Next, the flow of each of various types of information in the data management system of this preferred embodiment is described in detail using various types of information generated by an endoscopic examination as an example.

Figure 8:
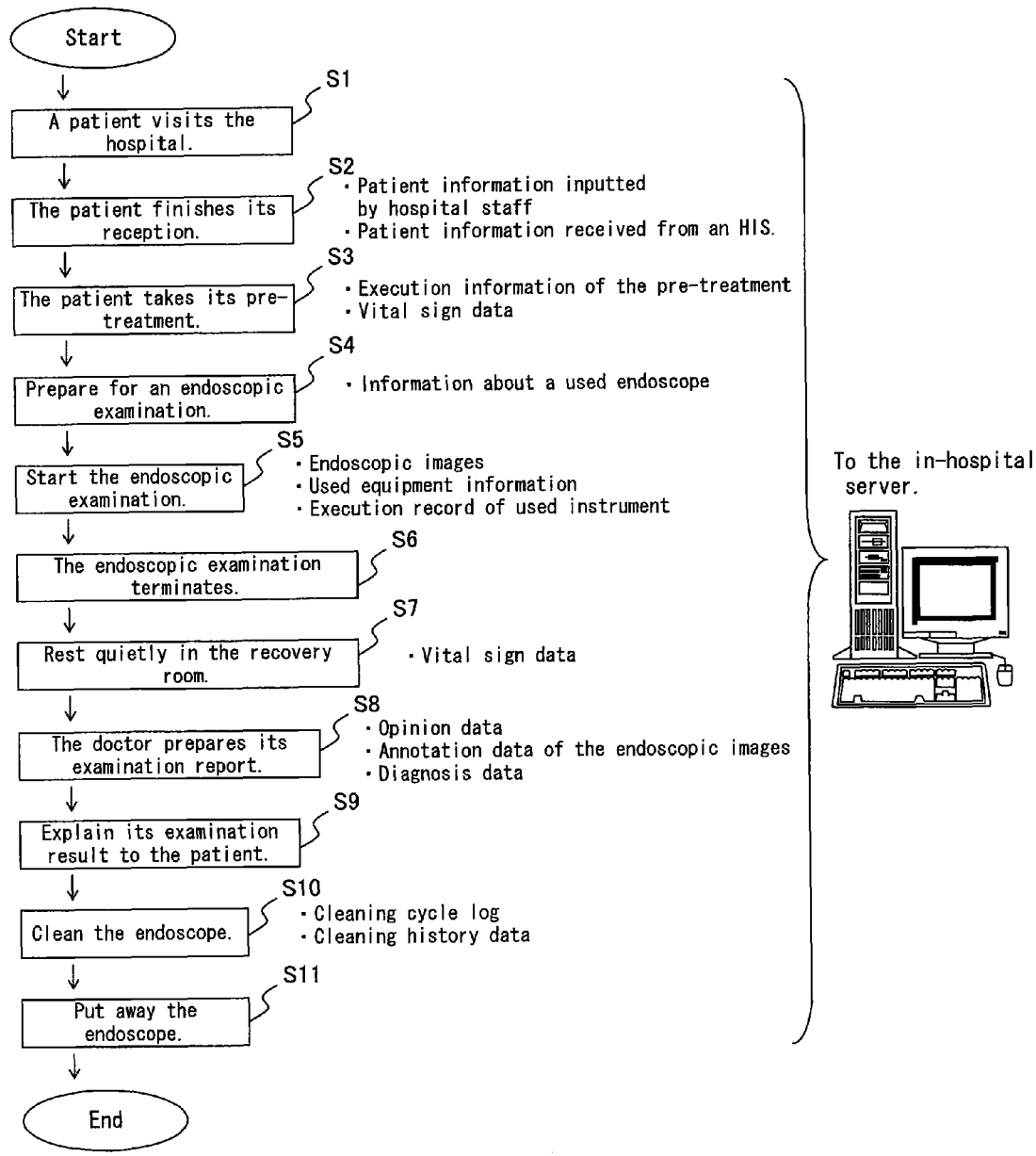
FIG. 8 shows the process flow in the hospital at the time of endoscopic examination and its major generated in-hospital information.

FIG. 8 shows the process flow in the hospital at the time of endoscopic examination and its major generated in-hospital information.

In FIG. 8, after in step S1 a patient visits the hospital and in step S2 the patient finishes its receiving procedures at the reception of a diagnosis and treatment department in which the patient takes diagnosis and treatment, patient information that hospital staff inputs from a terminal at the reception and patient information received from the HIS is stored in the in-hospital server of the diagnosis and treatment department.

Then, when in step S3 the temperature and pulse rate of the patient are measured as the pre-treatment of an endoscopic examination, these performance records and vital sign data, which is the measurement result, are inputted from the terminal and are recorded and stored in the in-hospital server.

When starting the endoscopic examination, as its preparation (step S4), information for specifying an examination instrument, such as an endoscopic device to be used and the like is inputted from the terminal. Then, at the time of examination (step S5), the image data of a sensed endoscopic image, information about used equipment, the performance record of a used instrument is transmitted from the examination device terminal to which each piece of equipment is connected to the in-hospital server. The in-hospital server stores the data in the database, and stores and accumulates it.

While the patient rests in a recovery room (step S7) after the endoscopic examination finishes (step S6), its temperature and pulse rate are measured. Then, these results are inputted from the terminal as vital sign data and are transmitted to the in-hospital server.

After the endoscopic examination finishes, in step S8 a doctor in charge prepares an examination report. When preparing this report, the opinion of a doctor, the annotation data of an endoscopic image sensed by examination, diagnosis data are inputted from the terminal and are transmitted to the in-hospital server. Then, in step S9 the examination result is explained to the patient.

In step S10, the instrument, such as an endoscope or the like, used for the endoscopic examination is cleaned by the endoscope cleaning device, and in step S11 the instrument is accommodated into a predetermined place. However, in this case, a cleaning cycle log and cleaning history data are transmitted to the in-hospital server as the record of this cleaning.

The in-hospital information shown in FIG. 8 is transmitted to the in-hospital server via the intra-hospital LAN from time to time. The in-hospital server stores the in-hospital information in the database, and stores and manages it. Then, the manager of the in-hospital server inputs mask information indicating whether the provision to outside the hospital of this in-hospital information is permitted to the in-hospital information. Thus, the external server sucks up only information whose external provision is permitted by this mask information.

Figure 9:
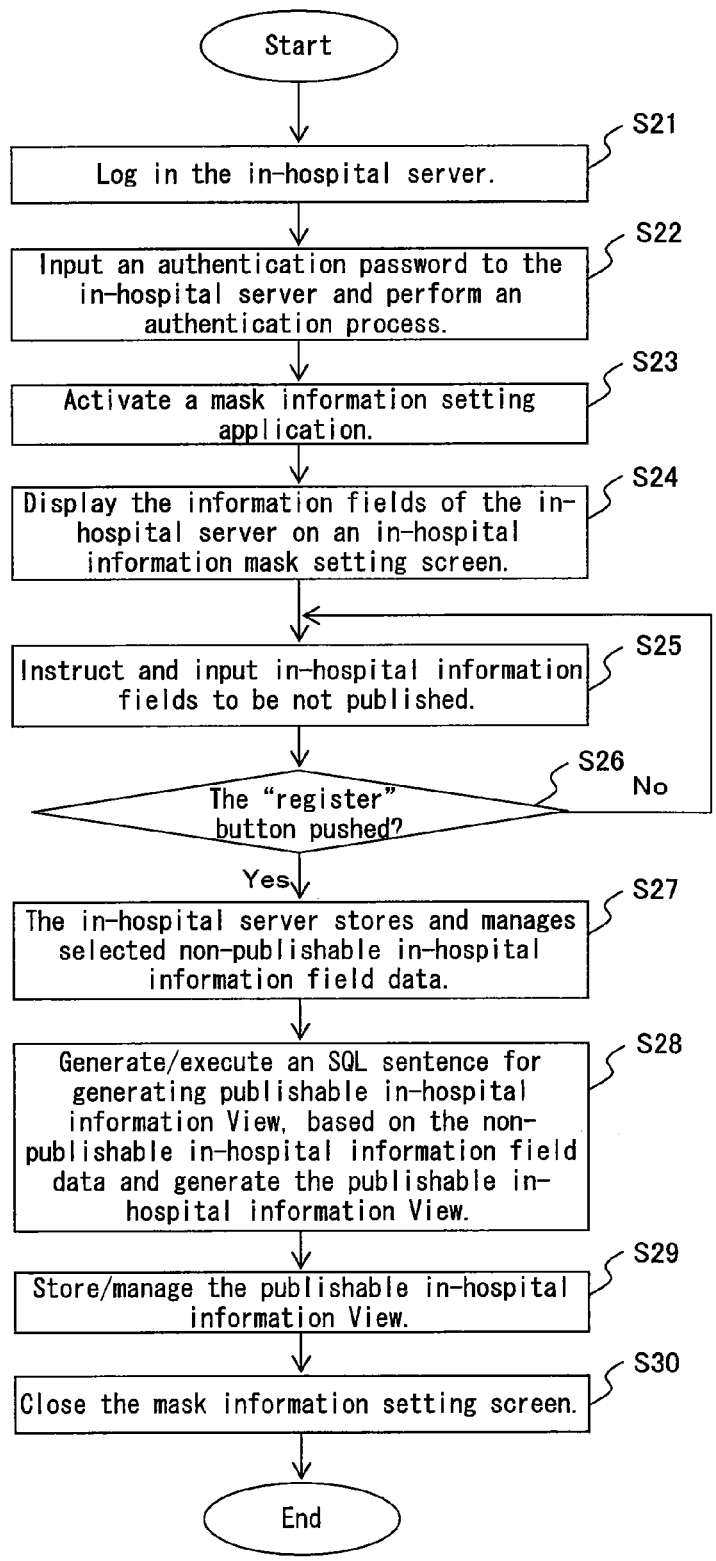
FIG. 9 is a flowchart showing the operational process of the in-hospital server at the time of mask information setting.

FIG. 9 is a flowchart showing the operational process of the in-hospital server at the time of mask information setting.

By this process, whether the external provision of the in-hospital information stored in the in-hospital server should be permitted is set in the in-hospital information.

In FIG. 9, in step S21 the manager of the in-hospital server logs in in-hospital server from the in-hospital server or a terminal connected to the in-hospital server via an in-hospital LAN.

Then, in step S22 the manager of the in-hospital server inputs an authentication password. Authentication information is referenced by the inputted password and an authentication process is performed. If no authentication permit is given, processes after that are terminated.

If in the authentication process of step S22 its authentication is permitted, then in step S23 the in-hospital server activates a mask information setting application.

This mask information setting application performs a mask information setting process of setting whether the external provision of the information recorded and stored in the in-hospital server should be permitted. In step S24, in the in-hospital server the mask information setting application activated in step S23 displays a mask information setting screen on which the field s of the in-hospital information stored in the in-hospital server is shown, on the monitor of the terminal logged in the in-hospital server in step S21. Then, in step S25 the manager of the in-hospital server selects the fields of information whose external provision is prohibited from the screen displayed in step S24 and inputs the fields.

Figure 10:
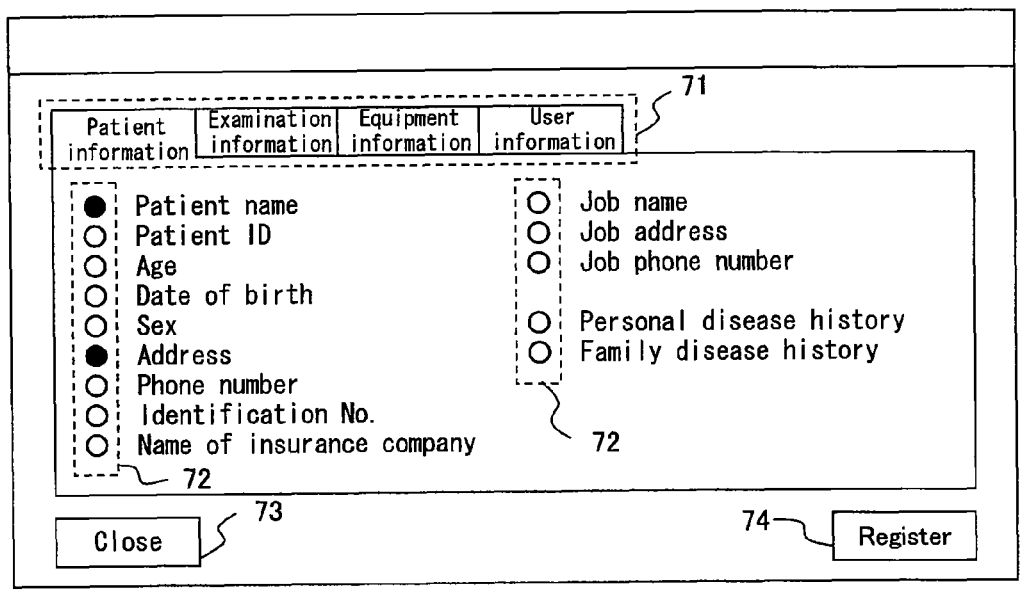
FIG. 10 shows an example of a mask information setting screen.

FIG. 10 shows an example of a mask information setting screen displayed in step S24.

On the screen shown in FIG. 10, the manager of the in-hospital server selects the field s of information whose external provision is prohibited from "patient information", "examination information", "equipment information" and "user information", by operating a pointing device or the like. Then, the manager selects information fields which should not be published from the detailed information field s of the selected tab 71 by checking a radio button 72 (a field marked with ● indicates the selected field in FIG. 10) and records the selected and specified contents by pushing a "register" button 74. Then, by pushing a "close" button 73, the setting of mask information is completed. The classification of the in-hospital information stored in the database in the in-hospital server into "patient information", "examination information", "equipment information" and "user information" is one example. The in-hospital information can be classified appropriately according to how to define the type of collected and stored information and the data structure of its database.

When the manager of the in-hospital server selects all information field s whose external provision should be prohibited on the mask information setting screen shown in FIG. 10 and pushes the "register" button 74 on the screen (yes in step S26), in step S27 the in-hospital server stores and manages non-publishable in-hospital information field data indicating the field s that are selected and inputted in step S25, as mask information.

Then, in step S28 the in-hospital server generates a definition sentence by the SQL code, for generating publishable in-hospital information View, based on the non-publishable in-hospital information field data stored in step S27 and executes the definition sentence to generate publishable in-hospital information View. Then, in step S30 the mask information setting screen is closed and this process is terminated.

FIG. 11 shows an example of in-hospital information stored in the in-hospital server on the basis of which View is generated in step S28.

FIG. 11 shows act.patient_table in which patient information is stored as its example. This act.patient_table has information field s to be classified as patient information in its column, and the column names of each information field, its Japanese name, its content character and numerical value data, which is not shown in FIG. 11, corresponding to the column are stored in its line. In this example, in-hospital data collected in the in-hospital server is stored in the database and is stored as act.patient_table, act.study_table, act.equipment_table and act.user_table corresponding to the above-described "patient information", "examination information", "equipment information" and "user information", respectively. Such a table structure is one example, and an appropriate structure can be taken according to how to define the type of collected and stored information and the data structure of a database.

FIG. 12 shows an example of a definition sentence by the SQL code, for generating publishable in-hospital information View generated in step S29.

The definition sentence shown in FIG. 12 defines how to generate the Views of "patient information", "examination information" and "equipment information" by SQL commands. A table in which the values of PatientID, Patient-Name, Age and the like whose publication is prohibited by the non-publishable in-hospital information field data stored in step S27 of FIG. 10, in the column of a "patient information" table act.patient_table are replaced with "- - - - -" is generated as Reft.patient_table. Since "examination information" and "equipment information" have no field s whose publication is prohibited by the non-publishable in-hospital information field data, act.study_table and act.equipment_table are generated as ref.study_table and ref.equipment_table, respectively, without performing any modification.

By executing the definition sentence by SQL, shown in FIG. 12, a View in which field s whose publication is prohibited are replaced with "- - - - -" is generated. By the external server sucking up this View from the in-hospital server, information whose publication is prohibited can be prevented from externally leaking.

Figure 13:
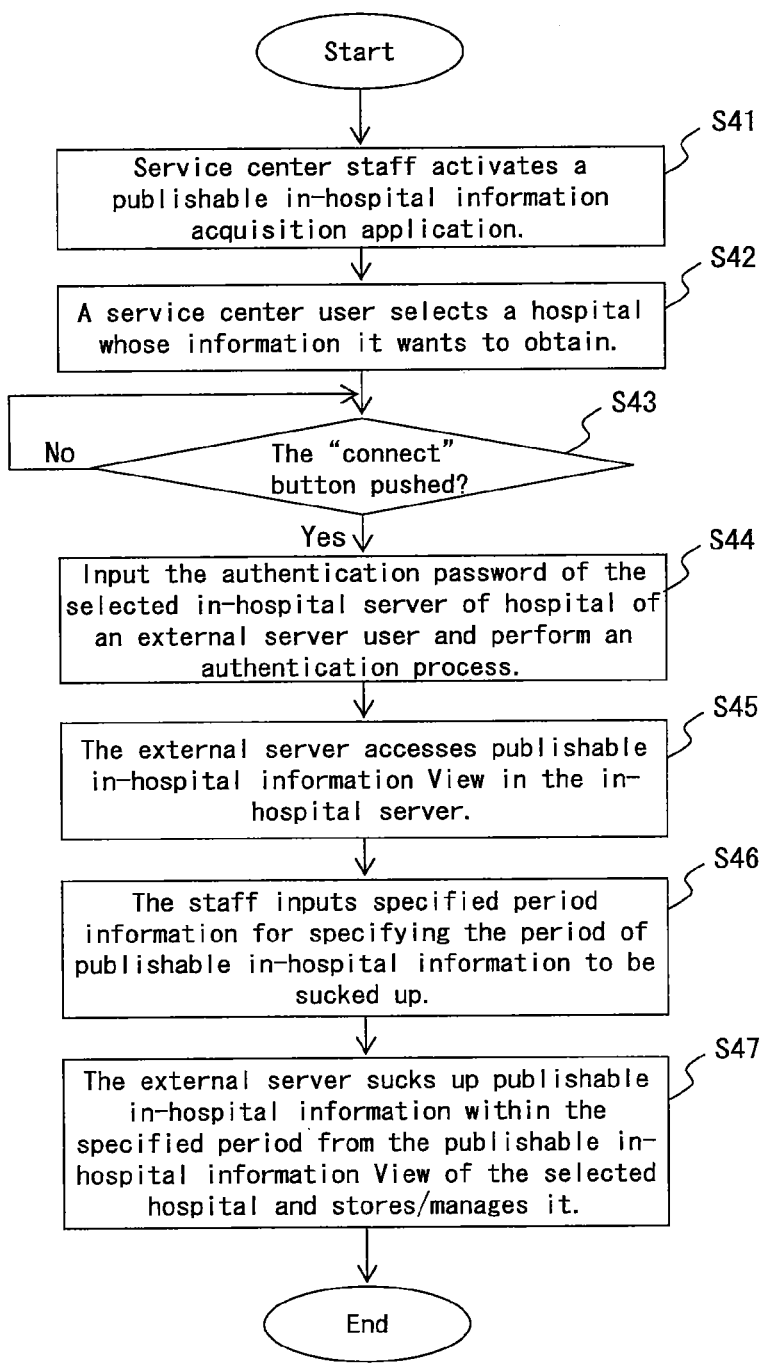
FIG. 13 is a flowchart showing the process of the external server, performed when sucking up information from the in-hospital server of a hospital.

FIG. 13 is a flowchart showing the process of the external server, performed when sucking up information from the in-hospital server of a hospital.

In FIG. 13 when the process is started, firstly in step S41 the staff of a facility, such as a service center activates a publishable in-hospital acquisition application of the external server. Then, this publishable in-hospital acquisition application sucks up information from each hospital using a network.

In step S42, this publishable in-hospital acquisition application displays a selection screen and the staff of a facility, such as a service center selects a hospital from which information is obtained (no in step S43).

Figure 14:
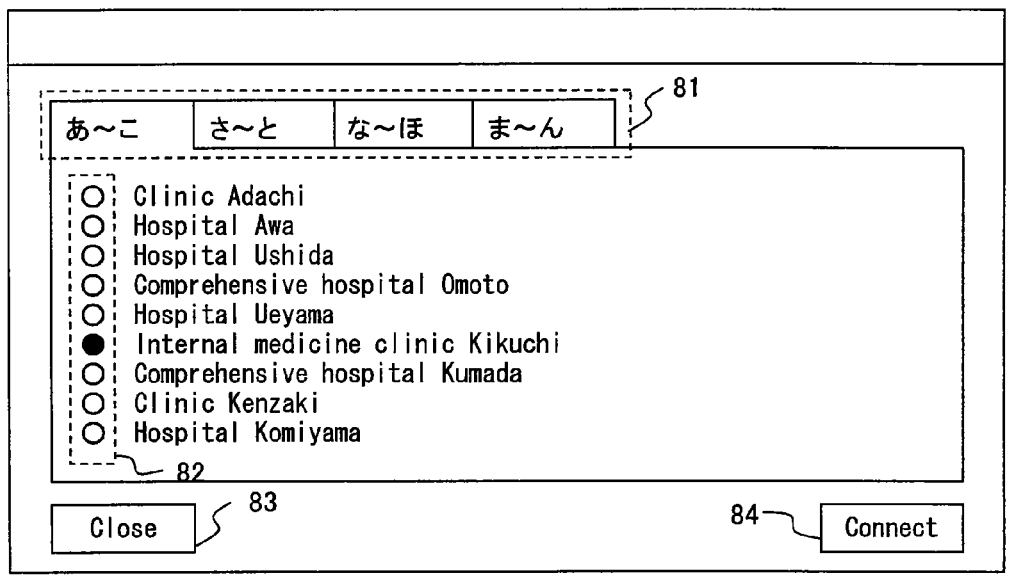
FIG. 14 shows an example of a hospital selection screen.

FIG. 14 shows an example of the hospital selection screen displayed on this time.

In FIG. 14, a tab 81 "あ〜こ", "さ〜と", "な〜ほ" and "ま〜ん" which classify hospital names in order of Japanese alphabet (あいうえお) is selected by operating a pointing device. Then, a target hospital name is selected from the hospital names shown in the selected tab 81 by checking the radio button 82 (a field marked with ● indicates the selected field). Then, the selected and specified contents are recorded by pushing a "connect" button 84. Then, the selection/specification of the operator is registered by pushing the "close" button 83, and the flow proceeds to the network connection process to a subsequent hospital.

When the staff of a facility, such as a service center, selects a hospital on the screen shown in FIG. 14 and pushes the "connect" button 84 (yes in step S43), then in step S44 the external server is connected to the selected one or plurality of hospital facilities via the network 61 or 62 shown in FIG. 7. Then, the staff inputs an authentication password for obtaining an authentication permit from the hospital selected in step S42 and transmits the password to the in-hospital server of a corresponding to make it perform an authentication process. Then, if the authentication permit can be obtained from the in-hospital server, in step S45 the external server accesses the publishable in-hospital information View that is generated by the in-hospital server in step S28 of FIG. 9 and is stored in the in-hospital server of the hospital.

Then, in step S46 in the external server, the staff specifies and inputs the period of a publishable in-hospital information to be sucked up from the in-hospital server. Then, in step S47 the publishable in-hospital information corresponding to the specified and inputted period is sucked up, and is stored and managed. If the external server is connected via the network 62, the network is disconnected and then this process is terminated.

FIG. 15 shows examples of the publishable in-hospital information sucked up from the hospital by the external server in step S47.

Of a plurality of pieces of publishable in-hospital information sucked up from the in-hospital server by the external server, one shown in FIG. 15A is in-hospital facility information indicating information about endoscopic equipment in the hospital and includes the respective types and numbers of upper endoscopes, lower endoscopes, video processors, treatment instruments used for an endoscope, vital sign monitors and endoscopic systems. One shown in FIG. 15B is examination information indicating information about an endoscopic examination conducted in a hospital includes the name of an examined patient, the date of its visit, an examination starting time, the type of an examination, the name and ID of a used endoscope, the number of sensed endoscopic images, the name of an examining doctor, the names of nurses, the name and number of a used treatment instrument and the name and number of a used medicine. One shown in FIG. 15C is facility information, being information about the maintenance of endoscopic equipment in a hospital and includes the name of a target facility, its date of purchase, its unit price, its used frequency, its date of failure, its repair company, its period of guaranty, its availability and the date of repair application. One shown in FIG. 15D is information about an endoscope cleaning machine and includes the name and ID of an endoscope cleaned by a cleaning machine, the name and ID of a cleaner, a cleaning starting time and various types of cleaning machine setting information at the time of cleaning and the like. One shown in FIG. 15E is in-hospital resources information, being information about endoscopic examination staff and equipment in a hospital and includes the respective numbers of endoscopic doctors, nurses and cleaners in charge, the number of examination per day, the total number of vital sign monitors, endoscopes and video processors.

If the plurality of pieces of information shown in FIG. 15 is related to the above-described classification of in-hospital information, the in-hospital facility information shown in FIG. 15A, the facility information shown in FIG. 15C and the cleaning machine information shown in FIG. 15D correspond to the equipment information, the examination information shown in FIG. 15B corresponds to the examination information and the in-hospital resources information shown in FIG. 15E corresponds to the user information.

In FIG. 15, since the publication of the name of a patient in the examination information is prohibited, in FIG. 15B its field is made "- - - - -" and the external server cannot read the patient name.

The publishable in-hospital information sucked up from a hospital by the external server can also be stored in the external server as rare data and each service application can process this rare data. Alternatively, the information sucked up by the external server can be processed in advance and each service application can read the data.

Figure 16:
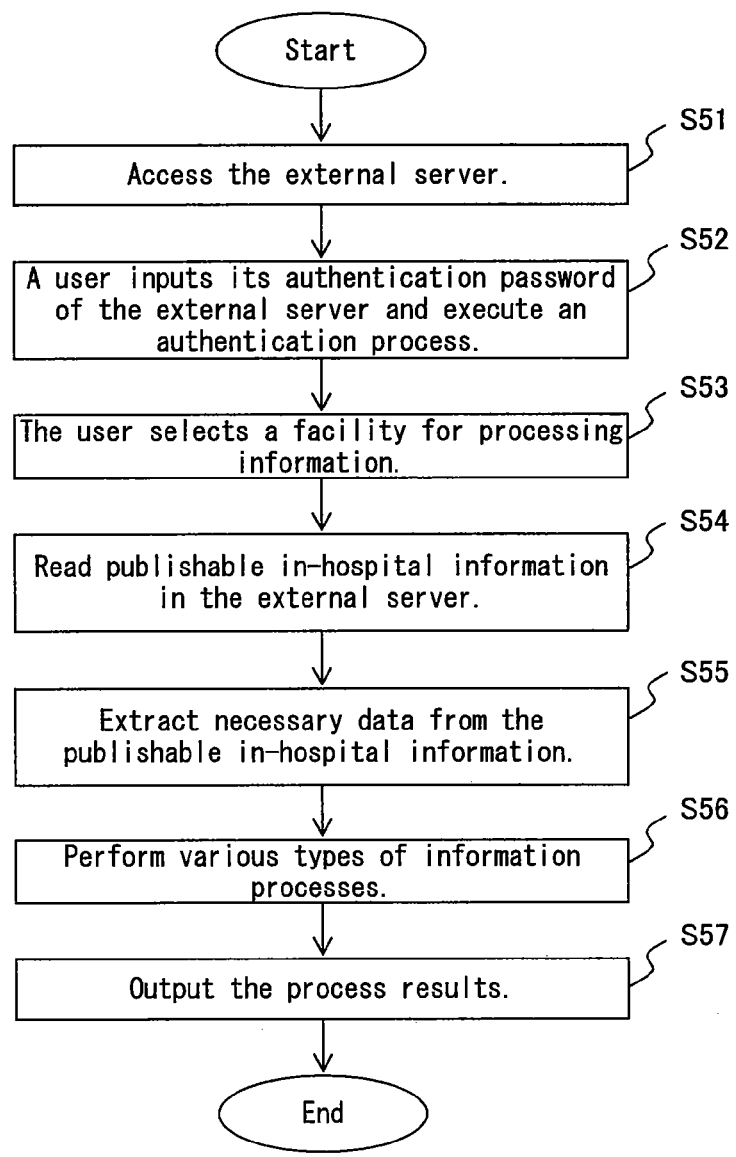
FIG. 16 is a flowchart showing the process of the service application.

FIG. 16 is a flowchart showing the process of each service application. This service application is executed in the terminal 56 connected to the intra-house LAN 51 in the external facility 50 shown in FIG. 7 or an information processing device connected to the external server 55 via the networks 61 and 62.

When the process shown in FIG. 16 is started, firstly in step S51 a terminal in which each service application operates accesses an external server via an intra-house LAN or the like.

Then, in step S52 a service application operating in the terminal makes a user to input an authentication password for obtaining an authentication permit to the external server and transmits the password to the external server to make the external server to perform an authentication process.

If in step S52 receiving the authentication permit from the external server, in step S53 the service application displays a selection screen on the terminal to make the user select a facility for conducting information processing.

Then, the service application reads the publishable in-hospital information recorded in and managed by the external server, and in step S55 extracts data needed to provide a service, from this publishable in-hospital information. Then, in step S56 the service application various types of processes corresponding to the service, using this data. Then, in step S57 the service application outputs the process result and this process is terminated.

As described above, according to the data management system in this preferred embodiment, a mechanism for efficiently sucking up necessary in-hospital information from outside the hospital and providing each service can be realized.

Since of the in-hospital information handled inside the hospital, only one whose external provision is permitted can be externally read out, information whose external provision is prohibited, such as personal information and the like can be prevented from leaking.

Furthermore, even when a new service using in-hospital information is added and the number of service applications for realizing its services increases, the situation can be easily coped with only by giving the minimum modifications to the existing function.

Although in the data management system in this preferred embodiment, the exchange of information between a hospital facility and an external facility, such as a service center or the like, is conducted via a network, the information can also be exchanged using a portable storage medium, such as a DVD or the like.

Although in-hospital information collected in the in-hospital server in a hospital is stored in the database, and stored and managed, this database can be built using not only SQL but also another data manipulation language.

There is also a conventional data management system in which a terminal installed in a hospital transmits in-hospital information indicating the used state of medical equipment to an information registration server (for example, corresponding to the out-hospital server (out-hospital information processing device) and the external server 55 shown in FIG. 7) installed in an external facility for providing a medical service, such as the rental service of medical equipment via a network as a communication line, and the information registration server or the like provides the hospital with a medical service by analyzing the in-hospital information, or charging a fee for the medical service (for example, see re-published WO02/017171 (pages 14~25, FIGS. 1~9)).

If an external facility provides a medical service, based on in-hospital information and charges a fee for the medical service thus, it is preferable to record a variety of in-hospital information on the information registration server in order for the external facility to provide a hospital with better services.

However, if the law of medical treatment is revised or the policy of a hospital is modified, sometimes part of in-hospital information cannot be transmitted to an information registration server or new in-hospital information can be transmitted to the information registration server.

If part of in-hospital information cannot be transmitted to an information registration server, better services must be provided to the hospital by transmitting in-hospital information other than the in-hospital information that cannot be transmitted, to the registration server to meet the revised law.

If new in-hospital information can be transmitted to the information registration server, the new in-hospital information can be added to the in-hospital information and be transmitted to the information registration server. Therefore, an external server can provide the hospital with better medical services.

In order to meet the revised law and the modified hospital policy to continue to provide better services thus, in-hospital information that is met by the revised law and the modified hospital policy and whose transmission to the information registration server is permitted must coincide with in-hospital information actually recorded in the information registration server.

Therefore, in order to reset information whose transmission from the hospital to the external facility is permitted to match in-hospital information recorded on the hospital with in-hospital information recorded in the external facility, conventionally the entire data management system commonly provided for the hospital and the external facility is replaced.

However, it takes much labor and cost to replace the entire data management system commonly provided for the hospital and the external facility.

Therefore, in the following preferred embodiments, a data management system capable of matching in-hospital information whose transmission to the external facility is permitted, according to the revised law and the modified hospital policy with in-hospital information actually recorded in the external facility while suppressing labor and cost is described.

Figure 17:
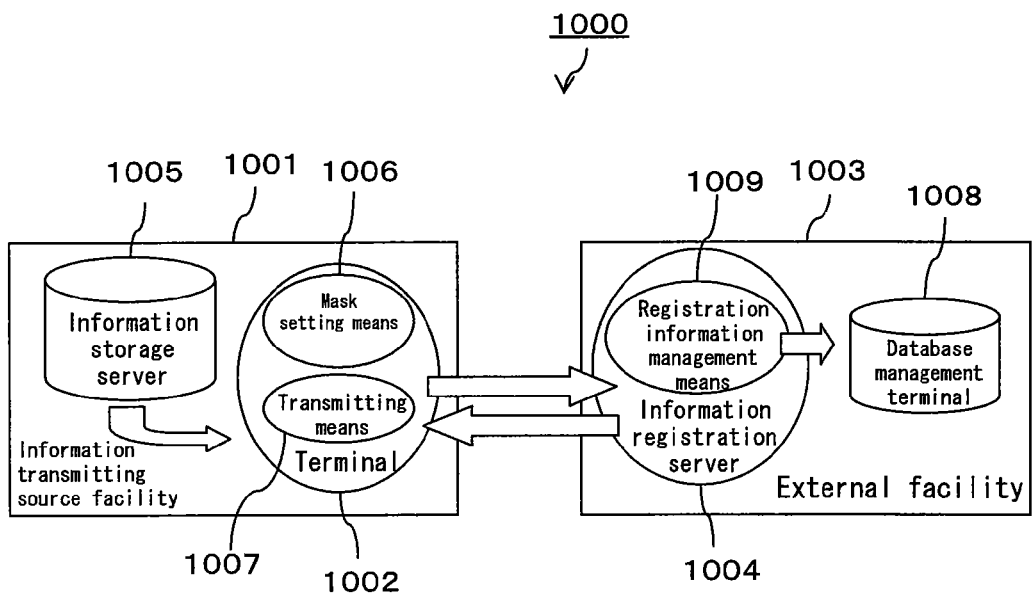
FIG. 17 shows the typical data management system of other preferred embodiments.

FIG. 17 shows a typical data management system capable of matching in-hospital information whose transmission to the external facility is permitted with in-hospital information actually recorded in the external facility.

The data management system 1000 shown in FIG. 17 comprises a terminal 1002 provided for an information transmitting source facility 1001 (this terminal 1002 (for example, corresponding to the in-hospital server (in-hospital information processing device) and the in-hospital server 45 shown in FIG. 7)) and an information registration server 1004 (for example, corresponding to the out-hospital server (out-hospital information processing device)) provided for an external facility 1003, which are connected via a network, such as the Internet or the like.

The terminal 1002 is connected to an information storage server 1005 provided for the information transmitting source facility 1001 via a network, such as a local area network (LAN) or the like.

The information storage server 1005 comprises a database (first database). On this database, a plurality of pieces of information (for example, corresponding to the patient information and endoscopic images, inputted by hospital staff, shown in FIG. 8) is recorded, and of the plurality of pieces of information, information based on a request from the terminal 1002 is transmitted to the terminal 1002. The database provided for the information storage server 1005 can also be provided for the terminal 1002.

The terminal 1002 comprises a mask setting means 1006 for relating field information indicating its field when the plurality of pieces of information recorded on the database of the information storage server 1005 is classified for each field to mask information indicating whether information corresponding to the field can be transmitted to the information registration server 1004 and recording them as a mask table and a transmitting means 1007 for transmitting modification information based on the mask table whose mask information is already modified to the information registration server 1004.

The transmitting means 1007 checks information whose transmission to the information registration server 1004 is permitted, based on a mask table set by the mask setting means 1006 and extracts the checked information from the database of the information storage server 1005. Then, the transmitting means 1007 transmits the information to the information registration server 1004.

The information registration server 1004 is connected to a database management terminal 1008 for recording the information transmitted from the terminal 1002 (for example, corresponding to information shown in FIGS. 15A~15E) via a network, such as a LAN or the like. The database management terminal 1008 comprises a database (second database) and records information transmitted from the information registration server 1004 to the database. The database management terminal 1008 can also comprise, for example, a personal computer or the like. The database provided for the database management terminal 1008 can also be provided for the information registration server 1004.

The information registration server 1004 comprises a registration information management means 1009 for requesting previous information which is information recorded on the database of the information storage server 1005 before the mask information is modified, of the plurality of pieces of information of the terminal 1002 and recording the information the database of the database management terminal 1008, or deleting the previous information already recorded in the database of the database management terminal 1008, based on the modification information transmitted from the terminal 1002.

The mask setting means 1006 and the transmitting means 1007 can also be realized by executing a program recorded on random-access memory (RAM), read-only memory (ROM) or the like provided for the terminal 1002 by a central processing unit (CPU) or the like.

The registration information management means 1009 can also be realized by a CPU or the like executing a program recorded, for example, on RAM, ROM or the like, provided for the information registration server 1004.

In the data management system 1000, when the mask information is modified, the previous information is recorded on the database of the database management terminal 1008, or the previous information already recorded on the database of the database management terminal 1008 is deleted.

Thus, information whose transmission from the terminal 1002 to the information registration server 1004 is permitted and information recorded on the database of the database management terminal 1008 can usually be matched.

Next, the case where the data management system 1000 is used as a data management system in which a terminal provided for a hospital and an information registration server provided for an external facility for providing medical services are connected via a network is studied.

Figure 18:
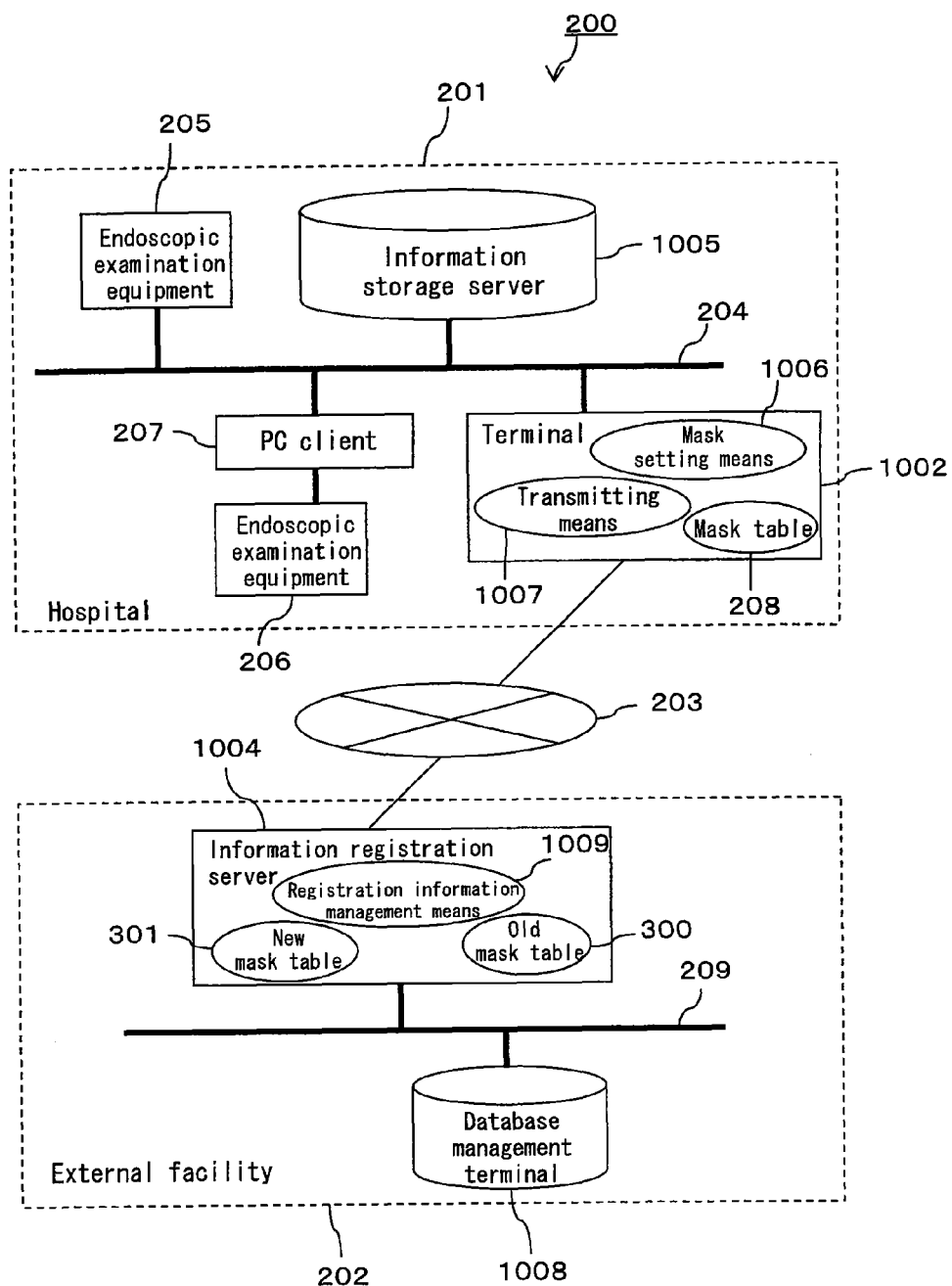
FIG. 18 shows the data management system of another preferred embodiment.

FIG. 18 shows the preferred embodiment in which the data management system 1000 is used as a data management system in which a terminal provided for a hospital and an information registration server provided for an external facility are connected via a network. The same reference numerals are attached to the same components as shown in FIG. 17.

The data management system 200 shown in FIG. 18 comprises the terminal 1002 provided for a hospital 201 and an information registration server 1004 provided for an external facility 202 for providing the hospital 201 with medical services, which are connected via a network 2003.

The terminal 1002 is connected to the information storage server 1005 via a network 204. The information storage server 1005 is connected to a personal computer (PC) client 207 (for example, corresponding to the examination device terminal 22) provided with an endoscopic examination equipment 205 and an endoscopic examination equipment 206 (for example, corresponding to the endoscopic examination device 21), via the network 204. In-hospital information indicating the examination results obtained by the endoscopic examination equipment 205 and 206 is transmitted from the endoscopic examination equipment 205 and the PC client 207 to the information storage server 1005 via the network 204 and is recorded on the database provided for the information storage server 1005.

The terminal 1002 comprises the mask setting means 1006 and the transmitting means 1007.

The mask setting means 1006 relates field information indicating its field when the plurality of pieces of information recorded on the database of the information storage server 1005 is classified for each field to mask information indicating whether information corresponding to the field can be transmitted to the information registration server 1004 and records them on the terminal 1002 as the mask table 208.

The transmitting means 1007 extracts in-hospital information from the database of the information storage server 1005, based on the mask table 208 and transmits the information to the information registration server 1004.

When the mask information is modified, the transmitting means 1007 transmits the mask table 28 whose mask information is already modified to the information registration server 1004.

The information registration server 1004 is connected to the database management terminal 1008 for recording the in-hospital information transmitted from the terminal 1002 via a network 209. The database management terminal 1008 comprises a database and records the in-hospital information transmitted from the information registration server 1004 to the database.

The information registration server 1004 comprises a registration information management means 1009 for recording the mask table 208 whose mask information is not yet modified and the mask table 208 whose mask information is already modified as an old mask table 300 and a new mask 301, respectively, and transmitting the in-hospital information transmitted from the terminal 1002 to the database management terminal 1008.

Figure 19:
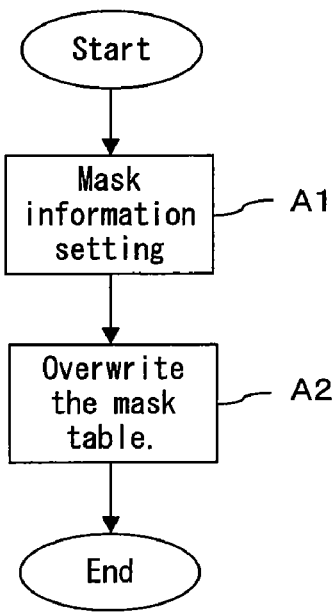
FIG. 19 is a flowchart showing the operation of a terminal.

FIG. 19 is a flowchart showing the operation of the terminal 1002.

Firstly, in step A1 the terminal 1002 relates each field to mask information indicating whether in-hospital information corresponding to the field should be transmitted to the information registration server 1004, based on the operation of a user, and sets a mask table (mask setting).

Figure 20:
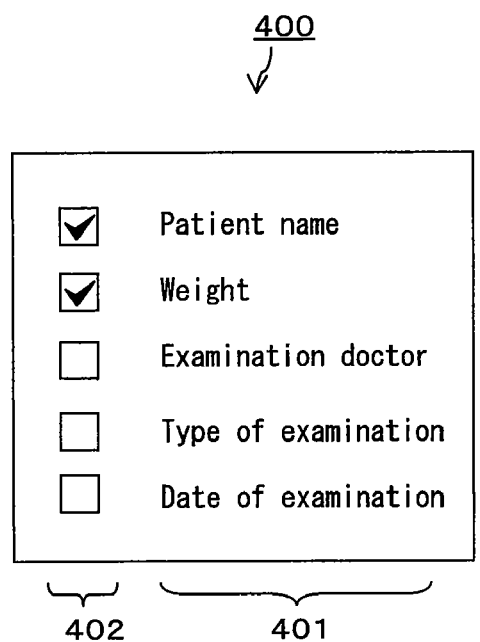
FIG. 20 shows an example of a mask setting GUI screen displayed on the monitor of the terminal.

FIG. 20 shows an example of a mask setting graphical user interface (GUI) screen displayed on the monitor or the like provided for the terminal 1002.

As shown in FIG. 20, the mask setting GUI screen 400 comprises a field display area 401 for displaying fields and a checkbox display area 402 for displaying a checkbox corresponding to each field.

In FIG. 20, checkboxes corresponding to "patient name" and "weight" are checked. A setting completion button or the like can also be provided on the mask setting GUI screen 400 and the mask setting can be terminated when the setting completion button is pushed.

When the user checks a checkbox, the transmission of the in-hospital information of fields corresponding to the checkboxes is prohibited. Specifically, in FIG. 20, since the checkboxes corresponding to "patient name" and "weight" are checked, the transmission to the information registration server 1004 of in-hospital information corresponding to "patient name" and "weight" is prohibited. The transmission to the information registration server 1004 of in-hospital information corresponding to the other fields "examination doctor", "examination type" and "date of examination" whose checkboxes are not checked is permitted. If the law is revised or the policy of the hospital 201 is modified and the transmission to the information registration server 1004 of in-hospital information corresponding to the field "examination doctor" is prohibited, the user checks a checkbox corresponding to the field "examination doctor".

FIG. 21 shows an example of the mask table 208 recorded on the terminal 1002. The mask table 208 shown in FIG. 21 corresponds to the mask setting of each checkbox of the mask setting GUI screen 400 shown in FIG. 20.

As shown in FIG. 21, the mask table 208 stores and comprises many mask information records 500 (500-1, 500-2, 500-3, 500-4, 500-5, . . . ). Each mask information record 500 comprises a field information area 501 for recording field information and a mask information area 502 for recording mask information indicating whether in-hospital information corresponding to field information should be transmitted to the information registration server 1004.

In FIG. 21, "examination doctor" and "not exist" are recorded in the field information area 501 and mask information area 502, respectively, of the mask information record 500-3. In FIG. 21, "exist" recorded in the mask information area 502 indicates that the transmission to the information registration server 1004 of in-hospital information is prohibited. In FIG. 21, "not exist" recorded in the mask information area 502 indicates that the transmission to the information registration server 1004 of in-hospital information is permitted.

Then, in step A2 of FIG. 19, when the user finishes the mask setting, the terminal 1002 writes the mask table 208 whose setting is finished over the mask table 208 used up to now and stores it.

Then, the terminal 1002 transmits the mask table 208 overwritten and stored to the information registration server 1004.

Figure 22:
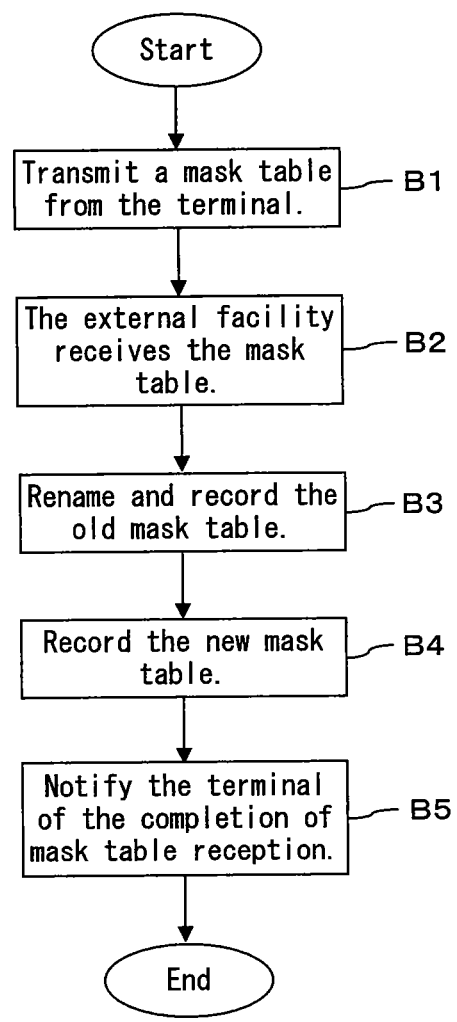
FIG. 22 is a flowchart showing a series of operations from the mask table transmitting operation of the terminal up to the mask table recording operation of an information registration server.

FIG. 22 is a flowchart showing a series of operations covering transmitting a mask table 208 from the terminal 1002 up to recording the mask table 208 on an information registration server 1004.

Firstly, in step B1, the terminal 1002 transmits the mask table 208 whose setting is finished to the information registration server 1004.

FIG. 23 shows an example of the mask table 208 whose setting is finished and which is transmitted to the information registration server 1004.

The mask table 208 shown in FIG. 23 is one in which "not exist" recorded in the mask information area 502 of the mask information record 500-3 in the mask table 208 shown in FIG. 21 is modified to "exist". In this case, characters "exist" recorded in the mask information area 502 of the mask information record 500-3 can be bold so that the modification of the mask information can be visually detected by the user. Alternatively, the characters can be emphasized by changing their style to italic, changing their color or so on.

After the mask table is set thus, the set mask table 208 is transmitted from the terminal 1002 to the information registration server 1004.

Figure 24:
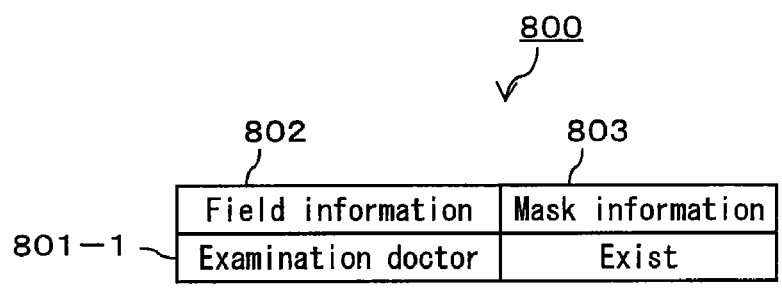
FIG. 24 shows another example of a mask table whose mask information is already modified.

FIG. 24 shows another example of the mask table 208 whose setting is finished and which is transmitted to the information registration server 1004. The mask table 800 shown in FIG. 24 is one in which characters recorded in the mask information area 502 of the mask information record 500-3 in the mask table 208 shown in FIG. 21 is modified from "not exist" to "exist" as in FIG. 23.

The mask table 800 shown in FIG. 24 comprises only mask information record 801 (801-1) whose mask information is already modified. The mask information record 801 comprises a field information area 802 for recording field information and a mask information area 803 for recording mask information indicating whether in-hospital information corresponding to field information should be transmitted to the information registration server 1004.

In FIG. 24, "examination doctor" and "exist" are recorded in the field information area 802 and mask information area 803, respectively, of the mask information record 801-1.

As described above, the mask table 800 can comprise only mask information record 801 whose mask information is already modified and be transmitted from the terminal 1002 to the information registration server 1004.

Then, in step B2 of FIG. 22, the information registration server 1004 receives the mask table 208 whose setting is finished.

Then, in step B3, the information registration server 1004 renames the old mask table 208 used up to now to record it as an old mask table 300.

Then, in step B4, the information registration server 1004 records the new mask table 208 whose setting is finished and is transmitted from the terminal 1002 as a new mask table 301.

Then, in step B5, the information registration server 1004 notifies the terminal 1002 of the reception completion of the mask table 208.

Thus, the information registration server 1004 records the old mask table 300 and the new mask table 301 and compares the new mask table 301 with the old mask table 300 to check which mask information is modified.

Then, the information registration server 1004 requests in-hospital information corresponding to the modified mask information of the terminal 1002, and transmits the information to the database management terminal 1008 or deletes it from the database of the database management terminal 1008.

FIG. 25 shows an example of a database provided for the database management terminal 1008.

The database 900 shown in FIG. 25 stores many in-hospital information records 901 (901-1, 901-2, 901-3, 901-4, 901-5, . . . ). Each in-hospital information record 901 comprises a field information area 902 for recording field information and an examination contents area 903 (903-1, 903-2, . . . ) for recording examination contents obtained by endoscopic examination equipment 205 and 206. The examination contents area 903 is added every time examination contents are transmitted from the terminal 1002. For example, it can be added in ascending order of date.

In FIG. 25, "examination doctor" and examination contents are recorded in the field information area 902 and examination contents areas 903-1 and 903-2, respectively, of the in-hospital information record 901-3. "○" shown in the examination contents area 903 indicates that some examination contents are recorded. "X" shown in the examination contents area 903 indicates that no examination contents are recorded. The database 900 shown in FIG. 25 which is provided for the information storage server 1005 records in-hospital information in all the examination contents areas 903.

Next, the operations of the registration information management means 1009 of comparing the old mask table 300 with the new mask table 301 and deleting in-hospital information corresponding to modified mask information from the database of the database management terminal 1008 are described.

Figure 26:
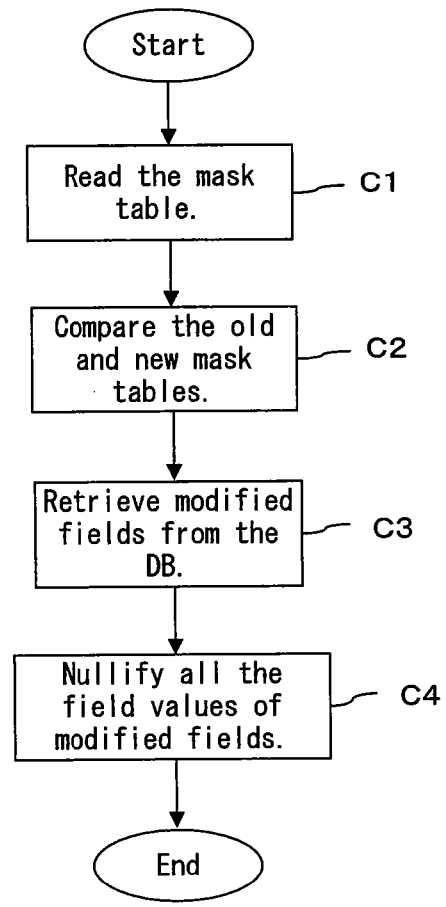
FIG. 26 is a flowchart showing the data management system in the case where in-hospital information corresponding to the modified mask information is deleted from the database of the database management terminal.

FIG. 26 is a flowchart showing the operations of the data management system 1000 in the case where in-hospital information corresponding to the modified mask information is deleted from the database of the database management terminal 1008.

Firstly, in step C1, the registration information management means 1009 reads the recorded old mask table 300 and new mask table 301.

Then, in step C2, the registration information management means 1009 compares the old mask table 300 with the new mask table 301.

FIG. 27 shows an example of the mask table in the case where the old mask table 300 and the new mask table 301 are combined in order to compare them. The mask table shown in FIG. 27 is obtained by combining the mask tables 208 shown in FIG. 21 and 23.

The mask table 1100 shown in FIG. 27 stores many mask information records 1100 (1101-1, 1101-2, 1101-3, 1101-4, 1101-5, ... ). Each mask information record 1101 comprises a field information area 1102 for recording field information, an old mask information area 1103 for recording the mask information of the old mask table 300 and a new mask information area 1104 for recording the mask information of the new mask table 301.

In FIG. 27, "examination doctor", "not exist" and "exist" are recorded in the field information area 1102, old mask information area 1103 and new mask information area 1104, respectively, in the mask information record 1101-3.

If "not exist" and "exist" are recorded in the old mask information area 1103 and new mask information area 1104, respectively, in the mask information record 1101 thus, the registration information management means 1009 determines that in-hospital information corresponding to the field information of the mask information record 1101 cannot be recorded on the database of the database management terminal 1008.

Then, in step C3 of FIG. 26, the registration information management means 1009 retrieves field information corresponding to the mask information whose modification is detected from the database of the database management terminal 1008.

Then, in step C4, the registration information management means 1009 nullifies all the filed values of examination contents area corresponding to the retrieved field information in the database of the database management terminal 1008.

FIG. 28 shows the database of the database management terminal 1008 in the case where all the examination contents areas corresponding to the modified mask information are nullified. The database shown in FIG. 28 is a part of the database 900 shown in FIG. 25.

The database 900 shown in FIG. 28 shows that in-hospital information recorded in all the examination contents areas 903 corresponding to the in-hospital information record 901-3 are deleted as a result of the comparison between the old mask table 300 and the new mask table 301 in the mask table 1100 shown in FIG. 27. Specifically, the database 900 shown in FIG. 28 shows that when in-hospital information to be recorded in the examination contents area 903-3 is transmitted from the terminal 1002 to the information registration server 1004, the mask information area 502 of the mask information record 500-3 in the mask table 208 shown in FIG. 21 is modified from "not exist" to "exist", the in-hospital information recorded in the examination contents areas 903-1 and 903-2 of the database of the database management terminal 1008 up to then has been deleted.

Thus, in-hospital information recorded on the database of the database management terminal 1008 can be deleted before the mask table 208 is modified.

In the database of the database management terminal 1008, the field values of all the examination contents areas corresponding to the retrieved field information can also be set in such a way as to be referenced, instead of nullifying the field values of all the examination contents areas corresponding to the retrieved field information.

Next, the operations of the registration information management means 1009 of comparing the new mask table 301 with the old mask table 300 and adding in-hospital information corresponding to the modified mask information to the database of the database management terminal 1008 are described.

Figure 29:
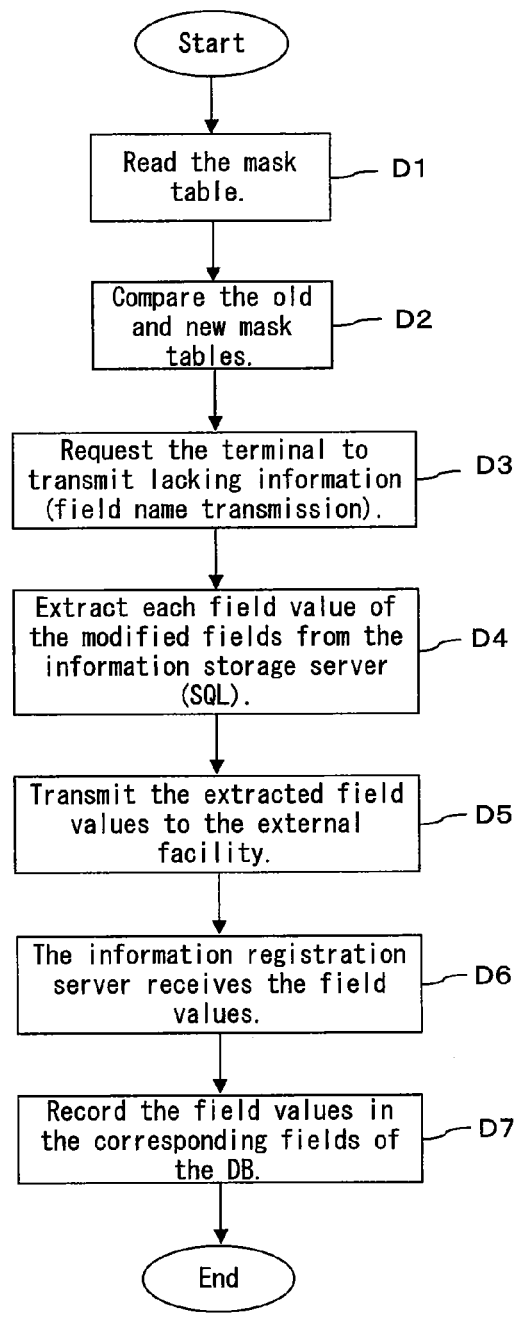
FIG. 29 is a flowchart showing the operation of additionally recording in-hospital information corresponding to the modified mask information on the database.

FIG. 29 is a flowchart showing the operation of additionally recording in-hospital information corresponding to the modified mask information to the database of the database management terminal 1008.

Firstly, in step D1, the registration information management means 1009 reads the recorded old mask table 300 and new mask table 301.

Then, in step D2, the registration information management means 1009 compares the new mask table 301 with the old mask table 300.

FIG. 30 shows an example of the mask table obtained by combining the old mask table 300 and new mask table 301 in order to compare the new mask table 301 with the old mask table 300.

The mask table 1400 shown in FIG. 30 stores many mask information records 1401 (1401-1, 1401-2, 1401-3, 1401-4, 1401-5, ... ). Each mask information record 1401 comprises a filed information area 1402 for recording field information, an old mask information area 1403 for recording the mask information of the old mask table 300 and a new mask information area 1404 for recording the mask information of the new mask table 301.

In FIG. 30, "weight", "exist" and "not exist" are recorded in the field information area 1402, old mask information area 1403 and new mask information area 1404, respectively, of the mask information record 1401-2.

If "exist" and "not exist" are recorded in the old mask information area 1403 and new mask information area 1404, respectively, of the mask information record 1401 thus, the registration information management means 1009 determines that in-hospital information corresponding to the field information of the mask information record 1401 can be recorded on the database of the database management terminal 1008.

Then, in step D3 of FIG. 29, the registration information management means 1009 requests lacking in-hospital information corresponding to the modified mask information of the terminal 1002. When requesting the lacking in-hospital information of the terminal 1002, an examination contents area 903 corresponding to the lacking in-hospital information can also be requested. As shown in FIG. 30, the registration information management means 1009 can also delete the entire mask information record 1401 in which "exist" and "not exist" are recorded in the old mask information area 1403 and the new mask information area 1404, respectively, from the database of the database management terminal 1008 and request the corresponding entire new mask information record 1401 of the terminal 1002.

Then, in step D4, the terminal 1002 extracts in-hospital information (field value) based on the request transmitted from the information registration server 1004 from the database of the information storage server 1005. In this case, as shown in FIG. 12, the in-hospital information can also be extracted by the structured query language (SQL), another database control language.

FIG. 31 shows the data table of the in-hospital information extracted from the database of an information storage server 1005. The data table shown in FIG. 31 records in-hospital information corresponding to the field information "weight".

The data table 1500 shown in FIG. 31 stores and comprises many lacking information records 1501 (1501-1, 1501-2, 1501-3, . . . ) for recording lacking in-hospital information. Each lacking information record 1501 comprises an examination contents area 1502 for recording examination contents and a weight area 1503 for recording weight.

In FIG. 31, "examination 1" and "68" are recorded in the examination contents area 1502 and weight area 1503, respectively, of the lacking information record 1501.

Then, in step D5 of FIG. 29, the terminal 1002 transmits the extracted in-hospital information to the information registration server 1004.

Then, in step D6, the information registration server 1004 receives the in-hospital information.

Then, in step D7, the information registration management means 1009 transmits the received in-hospital information to the database management terminal 1008 and records it on the database of the database management terminal 1008.

FIG. 32 shows how to additionally record the received in-hospital information on the database of the database management terminal 1008. The database 900 shown in FIG. 32 is a part of the database 900 shown in FIG. 25.

The database 900 shown in FIG. 32 the in-hospital information is additionally recorded in all the examination contents areas 903 corresponding to the in-hospital information record 901-2 as the result of comparison between the old mask table 300 and the new mask table 301 in the mask table 1400 shown in FIG. 30. Specifically, the database 900 shown in FIG. 32 indicates that when transmitting in-hospital information to be recorded in the examination contents area 903-3 from the terminal 1002 to the information registration server 1004, the mask information area 502 of the mask information record 500-2 in the mask table 208 shown in FIG. 21 is modified from "exist" to "not exist" and the in-hospital information recorded in the examination contents areas 903-1 and 903-2 in the database of the information storage server 1005 up to then has additionally recorded on the database of the database management terminal 1008.

Thus, in-hospital information recorded on the database of the information storage server 1005 can be additionally recorded on the database of the database management terminal 1008 in the mask table 208 is modified.

As described above, when the mask information is modified, the data management system 1000 records the previous information recorded on the database of the information storage server 1005 before the mask information is modified on the database of the database management terminal 1008 or deletes the previous information recorded on the database of the database management terminal 1008. Therefore, in-hospital information whose transmission from the terminal 1002 to the information registration server 1004 is permitted and in-hospital information actually recorded on the database of the database of the database management terminal 1008 can be always matched.

Thus, even when the in-hospital information law is revised or the hospital policy is modified, medical services and the like can be correctly analyzed. Since there is no need to replace the entire data management system, the labor and cost of building a data management system can be suppressed.

The present invention is not limited to the above-described preferred embodiments and various configurations in "claims" can be adopted. For example, the following configuration modification is possible.

Figure 33:
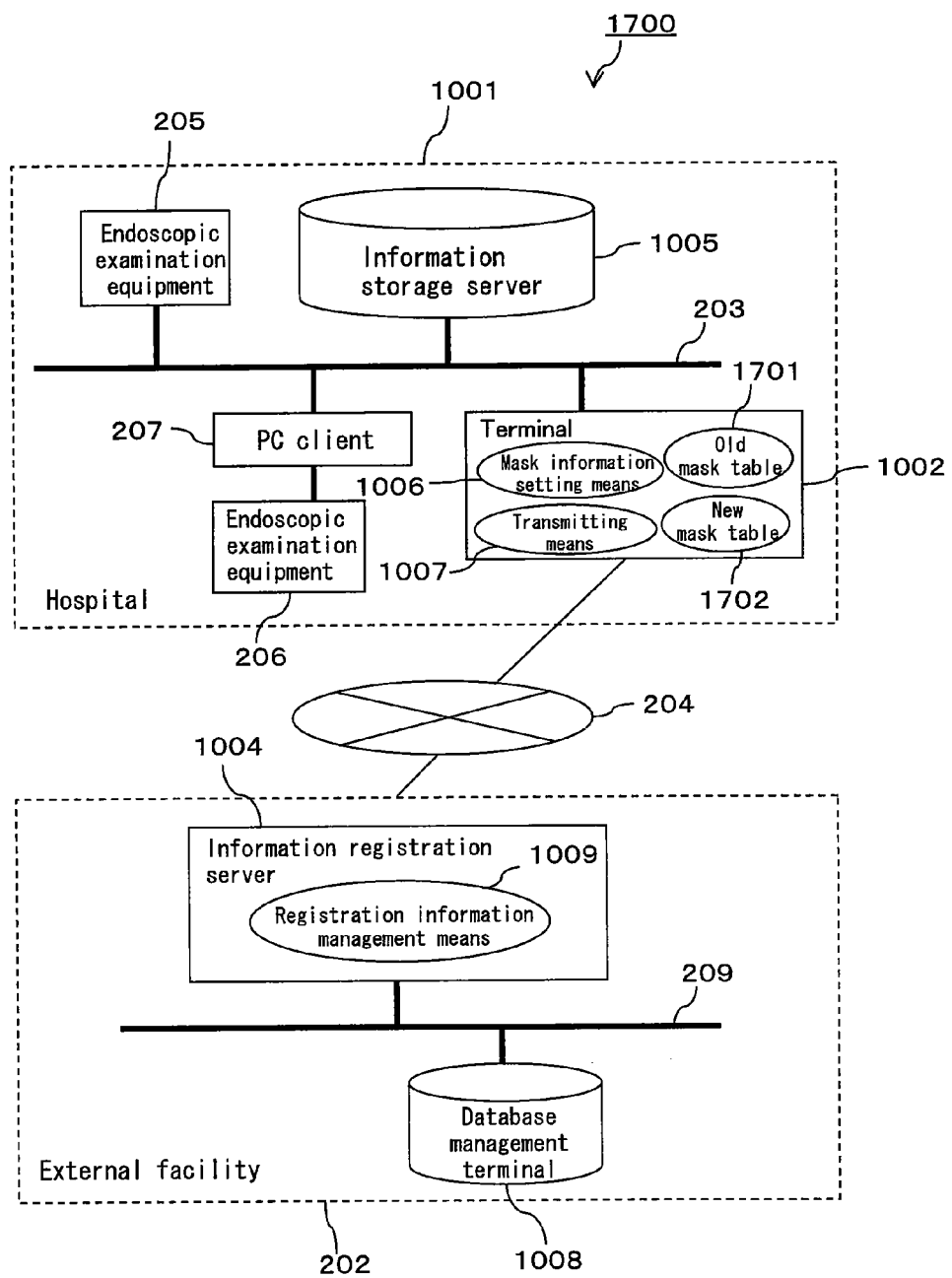
FIG. 33 shows the configuration of another preferred embodiment of the data management system.

FIG. 33 shows the configuration of another preferred embodiment of the data management system 1000. The same reference numerals are attached to the same components as shown in FIG. 18.

The data management system 1700 shown in FIG. 33 differs from the data management system 200 shown in FIG. 18 in that the transmitting means 1007 of the terminal 1002 compares a new mask table 1702 with an old mask table 1701 and if there is transmission-permitting mask information for modifying information whose transmission is prohibited to one whose transmission is permitted in the new mask table 1702, previous in-hospital information corresponding to the transmission-permitting mask information and an add instruction for additionally recording the previous in-hospital information corresponding to the transmission-permitting mask information for modifying information whose transmission is prohibited to one whose transmission is permitted to the database of the database management terminal 1008, the transmitting means 1007 transmits to the information registration server 1004. If there is transmission-prohibiting mask information for modifying information whose transmission is permitted to one whose transmission is prohibited in the new mask table 1702, a delete instruction for deleting the previous in-hospital information corresponding to the transmission-prohibiting mask information is deleted from the database of the database management terminal 1008 is transmitted to the information registration server 1004. The data management system 1700 also differs from the data management system 200 in that when the additional instruction is transmitted from the terminal 1002, the registration information management means 1009 of the information registration server 1004 additionally records previous in-hospital information corresponding to the transmission-permitting mask information to the database of the database management terminal 1008 and if a delete instruction is transmitted from the terminal 1002, the previous in-hospital information corresponding to the transmission-prohibiting mask information is deleted from the database of the database management terminal 1008.

Firstly, the operation of the terminal 1002 is described.

FIG. 34 is a flowchart showing the operation of the terminal 1002 of the data management system 1700.

Firstly, in step E1, the terminal 1002 relates each field to mask information indicating whether in-hospital information corresponding to the field should be transmitted to the information registration server 1004 by the operation of a user to set a mask table (mask setting).

Then, in step E2, the terminal 1002 renames the old mask table used up to now and records it as an old mask table 1701.

Then, in step E3, the terminal 1002 records the new mask table set in step E1 as a new mask table 1702.

Next, the operation of additionally recording in-hospital information corresponding to the modified mask information on the database of the database management terminal 1008 if there is modified mask information in the new mask table 1702 when the new mask table 1702 and the old mask table 1701 are compared is described.

Figure 35:
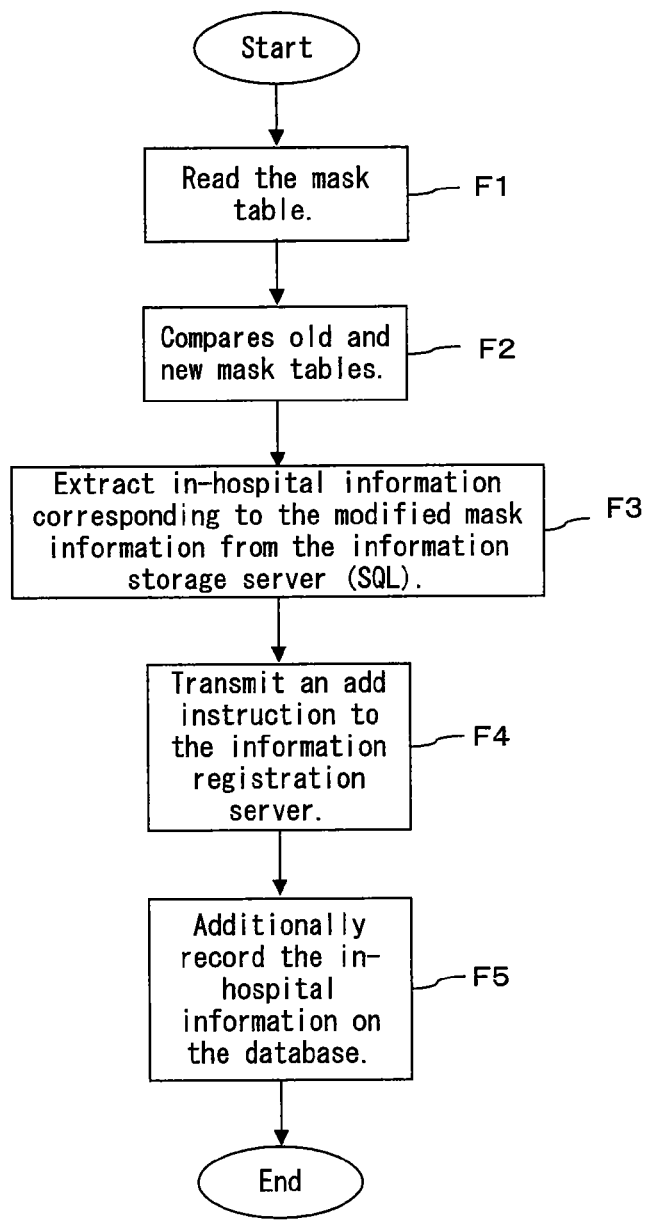
FIG. 35 is a flowchart showing the operation of the data management system, of additionally recording in-hospital information on the database.

FIG. 35 is a flowchart showing the operation of the data management system 1700, of additionally recording in-hospital information on the database of the database management terminal 1008.

Firstly, in step F1, the transmitting means 1007 of the terminal 1002 reads the recorded old mask table 1701 and new mask table 1702.

Then, in step F2, the transmitting means 1007 of the terminal 1002 compares the new mask table 1702 with the old mask table 1701.

Then, in step F3, the transmitting means 1007 of the terminal 1002 extracts in-hospital information corresponding to the modified mask information from the database of the information storage server 1005. The transmitting means 1007 of the terminal 1002 can also extracts in-hospital information recorded on the database of the information storage server 1005 before the mask information is modified, of all pieces of in-hospital information corresponding to the modified mask information from the database of the information storage server 1005. In-hospital information can also be extracted by an SQL or another database control language.

Then, in step F4, the transmitting means 1007 of the terminal 1002 transmits the extracted in-hospital information, an add instruction for additionally recording the in-hospital information on the database of the database management terminal 1008, and the recording destination of the database to the information registration server 1004.

Then, in step F5, upon receipt of the add instruction, the registration information management means 1009 of the information registration server 1004 transmits the in-hospital information and the recording destination of the database to the database management terminal 1008 and records the in-hospital information on the database of the database management terminal 1008, based on the recording destination of the database.

Next, the operations of the terminal 1002, of comparing the new mask table 1702 with the old mask table 1701 and deleting in-hospital information corresponding to the modified mask information from the database of the database management terminal 1008 are described.

Figure 36:
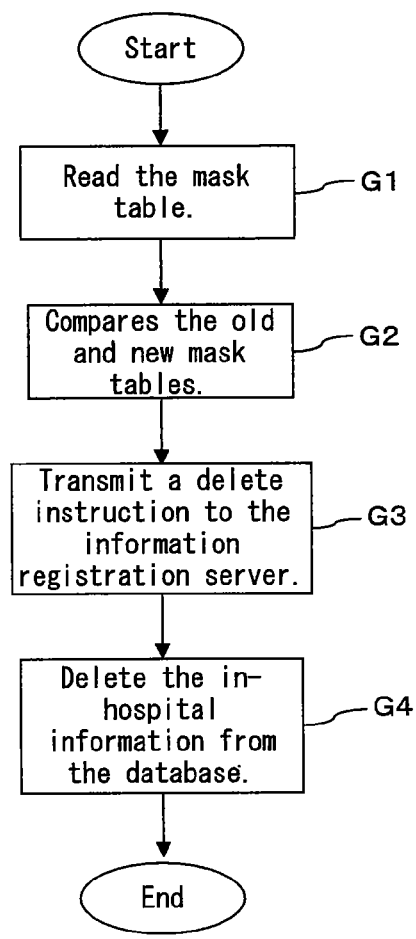
FIG. 36 is a flowchart showing the operation of the data management system, of deleting in-hospital information from the database.

FIG. 36 is a flowchart showing the operation of the data management system 1700, of deleting in-hospital information from the database of the database management terminal 1008.

Firstly, in step G1, the transmitting means 1007 of the terminal 1002 reads the recorded old mask table 1701 and new mask table 1702.

Then, in step G2, the transmitting means 1007 of the terminal 1002 compares the new mask table 1702 with the old mask table 1701.

Then, in step G3, the transmitting means 1007 of the terminal 1002 transmits a delete instruction for deleting in-hospital information corresponding to the modified mask information from the database of the database management terminal 1008, to the information registration server 1004.

Then, in step G4, the registration information management means 1009 of the information registration server 1004 delete in-hospital information from the database of the database management terminal 1008, based on the received delete instruction. In the database of the database management terminal 1008, in-hospital information corresponding to the modified mask information can also be set not to be referenced, instead of deleting the in-hospital information corresponding to the modified mask information.

As in this data management system 1700, the terminal 1002 can also determine whether in-hospital information recorded on the database of the information storage server 1005 before the mask information is modified should be recorded on the database of the database management terminal 1008.

Next, a data management system in another preferred embodiment (hereinafter called "another data management system") is described.

This other data management system differs from the data management system 1000 shown in FIG. 18 in that the transmitting means 1007 of the terminal 1002 transmits an instruction for recording previous in-hospital information recorded on the database of the information storage server 1005 before the mask information is modified, of a plurality of pieces of in-hospital information recorded on the database of the information storage server 1005 and an add instruction for recording additionally record the previous in-hospital information for deleting the previous in-hospital information to be recorded on the database of the database management terminal 1008, or a delete instruction for deleting the previous in-hospital information to be recorded on the database of the database management terminal 1008, without comparing the old and new mask tables and in that if the terminal 1002 transmits an add instruction, the registration information management means 1009 records the previous in-hospital information on the database of the database management terminal 1008 and if the terminal 1002 transmits a delete instruction, the registration information management means 1009 deletes the previous in-hospital information to be recorded on the database of the database management terminal 1008.

Next, the operation of additionally recording in-hospital information corresponding to the modified mask information on the database of the database management terminal 1008 in this other data management system is described.

Figure 37:
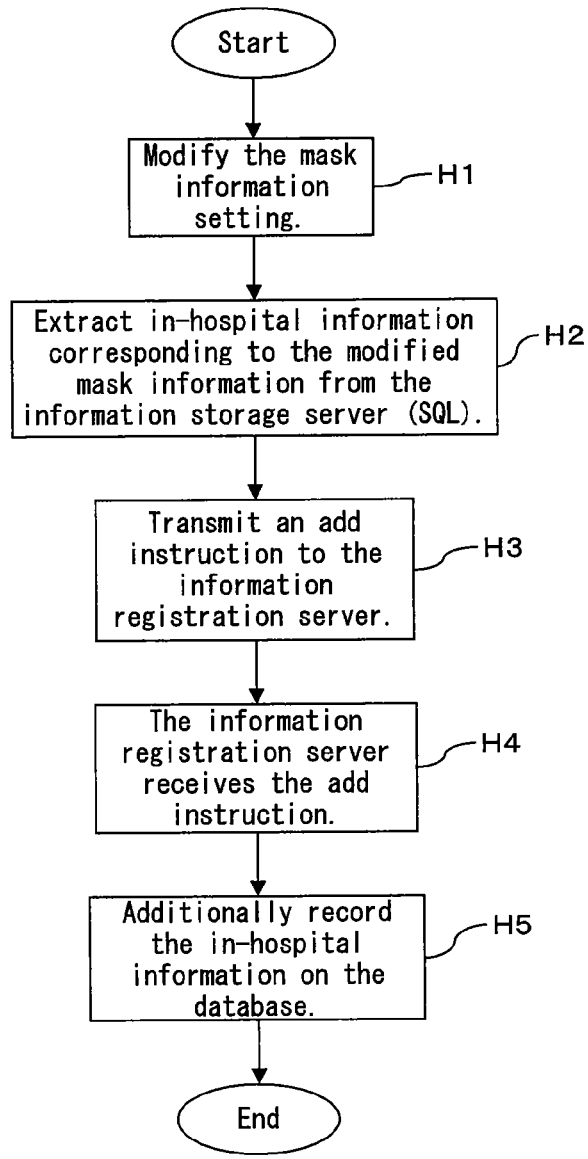
FIG. 37 is a flowchart showing the operation of the data management system, of additionally recording in-hospital information on the database.

FIG. 37 is a flowchart showing the operation of this other data management system, of additionally recording in-hospital information on the database of the database management terminal 1008.

Firstly, in step H1, each field is related to mask information indicating whether in-hospital information corresponding to the field should be transmitted to the information registration server 1004 as a mask table by the operation of a user to modify specific mask information.

Then, in step H2, the terminal 1002 extracts in-hospital information corresponding to the modified mask information from the database of the information storage server 1005. The terminal 1002 can also extract in-hospital information recorded on the database of the information storage server 1005 before the mask information is modified, of all pieces of in-hospital information corresponding to the modified mask information from the information storage server 1005. In-hospital information can also be extracted by an SQL and another database control language.

Then, in step H3, the terminal 1002 transmits the extracted in-hospital information, an add instruction for additionally recording the in-hospital information on the database of the database management terminal 1008 and the recording destination (field name) of the database to the information registration server 1004. The terminal 1002 can also transmits the extracted in-hospital information, the add instruction for additionally recording the in-hospital information on the database of the database management terminal 1008 and the recording destination (field name) of the database to the information registration server 1004 on a list.

Then, in step H4, the information registration server 1004 receives the in-hospital information, the add instruction and the recording destination of the database that are transmitted from the terminal 1002.

Then, in step H5, upon receipt of the add instruction, the registration information management means 1009 of the information registration server 1004 transmits the in-hospital information and the recording destination of the database to the database management terminal 1008 and records the in-hospital information on the database of the database management terminal 1008, based on the recording destination of the database.

Next, the operation of this other data management system, of deleting in-hospital information corresponding to the modified mask information from the database of the database management terminal 1008 is described.

Figure 38:
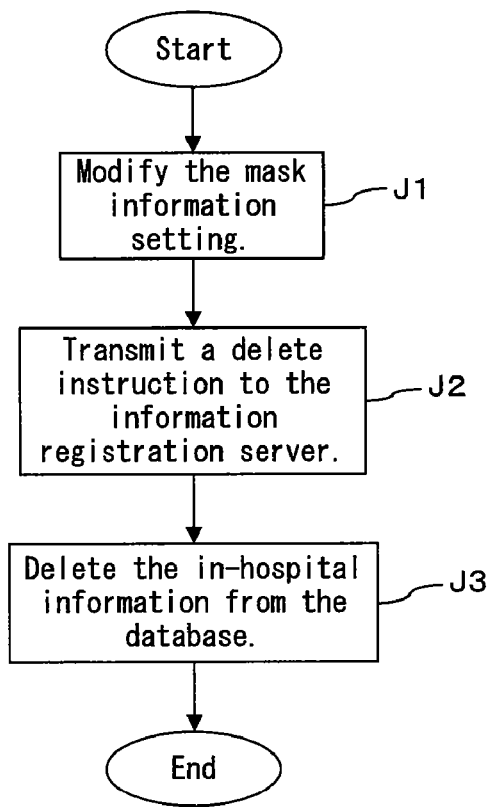
FIG. 38 is a flowchart showing the operation of the data management system, of deleting in-hospital information from the database.

FIG. 38 is a flowchart showing the operation of this other data management system, of deleting in-hospital information from the database of the database management terminal 1008.

Firstly, in step J1, each field is related to mask information indicating whether in-hospital information corresponding to the field should be transmitted to the information registration server 1004 as a mask table by the operation of a user to modify specific mask information.

Then, in step J2, the terminal 1002 transmits a delete instruction deleting in-hospital information corresponding to the modified mask information from the database of the database management terminal 1008 to the information registration server 1004.

Then, in step J3, the registration information management means 1009 of the information registration server 1004 deletes the in-hospital information from the database of the database management terminal 1008, based on the delete instruction transmitted from the terminal 1002. In the database of the database management terminal 1008, in-hospital information corresponding to the modified mask information can also be set not to be referenced, instead of deleting the in-hospital information corresponding to the modified mask information.

As in this other data management system, it can also be determined whether the in-hospital information corresponding to the modified mask information should be recorded on the database of the database management terminal 1008 without comparing the old and new mask tables.

Alternatively, in the above-described preferred embodiment, each of the terminal 1002 and the information registration server 1004 can be provided with a correspondence table relating field information to a simple symbol, such as a figure or the like and recording them. In this case, when the terminal 1002 transmits in-hospital information to the information registration server 1004, the simple symbol can be transmitted instead of the field information and the information registration server 1004 can refer to the correspondence table.

By transmitting the simple symbol instead of the field information thus when transmitting in-hospital information, the amount of information to be transmitted can be reduced.

In the above-described preferred embodiment, in-hospital information can also be added to and recorded on the database of the database management terminal 1008 and then the fact can also be returned to the terminal 1002.

Alternatively, in the above-described preferred embodiment, after in-hospital information is deleted from the database of the database management terminal 1008, such a notice can be returned to the terminal 1002.

Although in the above-described preferred embodiment, when a mask table is modified, the contents of the database of the database management terminal 1008 are updated, the currently used mask table and the contents of the database of the database management terminal 1008 can also be compared in intervals of a prescribed elapsed time and the contents of the database of the database management terminal 1008 can be updated based on the comparison result.

Thus, according to the above-described preferred embodiment, when mask information is modified, previous information is recorded on the database of the information registration server 1004 or previous information recorded on the database is deleted. Therefore, information whose transmission from the terminal 1002 to the information registration server 1004 is permitted can be always matched with information recorded on the database of the information registration server 1004.

By providing the terminal 1002 and the information registration server 1004 for the hospital 201 and the external facility 202 for providing medical services, even when the medical law is revised or the policy of the hospital 202 on which in-hospital information should be stored outside the hospital 202 is modified, in-hospital information whose transmission from the terminal 1002 to the information registration server 1004 is permitted and in-hospital information recorded on the database of the information registration server 1004 can be always matched. Therefore, a medical service for analyzing in-hospital information recorded on the database and providing the hospital 202 with it can be correctly realized.

In this case, since there is no need to replace the entire data management system, the labor and cost of re-building a database handled in the data management system can be suppressed.

What is claimed is:

1. A data management system with a terminal installed in an information transmitting source facility and an information registration server installed in an external facility, wherein the terminal comprises:

a first database for recording a plurality of pieces of information, mask setting means for relating field information indicating a field when the plurality of pieces of information are classified for each field, with transmission-permitting mask information indicating that information corresponding to the field can be transmitted to the information registration server, and with transmission-prohibiting mask information indicating that the information corresponding to the field cannot be transmitted to the information registration server, and said mask setting means also being configured for recording these pieces of related information as a mask table, and transmitting means for transmitting the mask table after modification to the information registration server via a network, when the transmission-permitting mask information or the transmission-prohibiting mask information corresponding to a certain field have been modified, and the information registration server comprises:

a second database for recording the plurality of pieces of information, recording means for recording, when the mask table is received, a mask table which was recorded before the reception of the mask table as an old mask table and for recording the received mask table as a new mask table, registration information management means for comparing the old mask table and the new mask table, for, if there is a field having been changed from a field corresponding to the transmission-prohibiting mask information into a field corresponding to the transmission-permitting mask information, receiving information corresponding to this changed field from the terminal so as to record it on the second database, and for, if there is a field having been changed from a field corresponding to the transmission-permitting mask information into a field corresponding to the transmission-prohibiting mask information, deleting information corresponding to this changed field from the second database.

2. A data management system with a terminal installed in an information transmitting source facility and an information registration server installed in an external facility, wherein the terminal comprises:

a first database for recording a plurality of pieces of information, mask setting means for relating field information indicating a field when the plurality of pieces of information are classified for each field, with transmission-permitting mask information indicating that information corresponding to the field can be transmitted to the information registration server, and with transmission-prohibiting mask information indicating that the information corresponding to the field cannot be transmitted to the information registration server, and said mask setting means also being for recording these pieces of related information as a mask table, and recording means for recording the mask table before modification and the mask table after the modification as an old mask table and a new mask table, respectively, when the transmission-permitting mask information or the transmission-prohibiting mask information corresponding to a certain field is modified, and transmitting means for comparing the old and new mask tables; for transmitting, if there is a field having been changed from a field corresponding to the transmission-prohibiting mask information into a field corresponding to the transmission-permitting mask information, to the information registration server, an add instruction for recording the previous information corresponding to this changed field on a second database within the information registration server; and for transmitting, if there is a field having been changed from a field corresponding to the transmission-permitting mask information into a field corresponding to the transmission-prohibiting mask information, to the information registration server a delete instruction for deleting information corresponding to this changed field from the second database, and wherein the information registration server comprises:

the second database, registration information management means for receiving, from the terminal, information corresponding to a field indicated by the add instruction so as to record it on the second database if the add instruction is transmitted from the terminal, and for deleting, from the second database, information corresponding to a field indicated by the delete instruction, if the delete instruction is transmitted from the terminal.

3. An information registration server in a data management system with a terminal and an information registration server installed in an external facility, the terminal comprising: a first database for recording a plurality of pieces of information; mask setting means for relating field information indicating a field when the plurality of pieces of information are classified for each field, transmission-permitting mask information indicating that information corresponding to the field can be transmitted to an information registration server, and transmission-prohibiting mask information indicating that the information corresponding to the field cannot be transmitted to the information registration server, and for recording these pieces of related information as a mask table; and transmitting means for transmitting the mask table after modification to the information registration server via a network, when the transmission-permitting mask information or the transmission-prohibiting mask information corresponding to a certain field is modified, wherein the information registration server comprises:

a second database for recording the plurality of pieces of information;

recording means for recording, when the mask table is received, a mask table having been recorded since before the reception of the mask table as an old mask table and recording the received mask table as a new mask table, and registration information management means for comparing the old mask table and the new mask table; for receiving, if there is a field having been changed from a field corresponding to the transmission-prohibiting mask information into a field corresponding to the transmission-permitting mask information, information corresponding to this changed field from the terminal so as to record it on the second database; and for deleting, if there is a field having been changed from a field corresponding to the transmission-permitting mask information into a field corresponding to the transmission-prohibiting mask information, information corresponding to this changed field from the second database.

4. A terminal in a data management system comprising the terminal and an information registration server installed in an external facility, the terminal being installed in an information transmitting source facility, wherein the terminal comprises:

a first database for recording a plurality of pieces of information;

mask setting means for relating field information indicating a field when the plurality of pieces of information are classified for each field, transmission-permitting mask information indicating that information corresponding to the field can be transmitted to the information registration server, and transmission-prohibiting mask information indicating that the information corresponding to the field cannot be transmitted to the information registration server, and for recording these pieces of related information as a mask table;

recording means for recording the mask table before modification and the mask table after the modification as an old mask table and a new mask table, respectively, when the transmission-permitting mask information or the transmission-prohibiting mask information corresponding to a certain field is modified, and transmitting means for comparing the old and new mask tables; for transmitting, if there is a field having been changed from a field corresponding to the transmission-prohibiting mask information into a field corresponding to the transmission-permitting mask information, to the information registration server an add instruction for recording information corresponding to this changed field on a second database in the information registration server; and for transmitting, if there is a field having been changed from a field corresponding to the transmission-permitting mask information into a field corresponding to the transmission-prohibiting mask information, to the information registration server a delete instruction for deleting information corresponding to this changed field from the second database.

5. An information registration method used in a system in which a plurality of pieces of information are transmitted from a terminal provided with a first database which is installed in an information transmitting source facility to an information registration server provided with a second database which is installed in an external facility via a network, wherein the method comprises the steps of:

relating via the terminal field information indicating a field when the plurality of pieces of information are classified for each field, with transmission-permitting mask information indicating that information corresponding to the field can be transmitted to the information registration server, and with transmission-prohibiting mask information indicating that the information corresponding to the field cannot be transmitted to the information registration server, and recording these pieces of related information into mask recording means as a mask table, transmitting via the terminal the mask table after modification to the information registration server via a network, when the transmission-permitting mask information or the transmission-prohibiting mask information corresponding to a certain field is modified, when the mask table is received, recording via the information registration server into recording means, a mask table having been recorded since before the reception of the mask table as an old mask table, and recording the received mask table into the recording means as a new mask table, comparing via the information registration server the old mask table and the new mask table; if there is a field that changed from a field corresponding to the transmission-prohibiting mask information into a field corresponding to the transmission-permitting mask information, receiving via the information registration server information corresponding to this changed field from the terminal so as to record it on the second database; and if there is a field having been changed from a field corresponding to the transmission-permitting mask information into a field corresponding to the transmission-prohibiting mask information, delegating via the information registration server information corresponding to this changed field from the second database.

6. A non-transient computer-readable recording medium with a program for enabling a computer to execute a process recorded thereon, the program being configured to effect the process and comprising:

relating field information indicating a field when a plurality of pieces of information recorded on a first database within a terminal are classified for each field, transmission-permitting mask information indicating that information corresponding to the field can be transmitted to an information registration server, and transmission-prohibiting mask information indicating that the information corresponding to the field cannot be transmitted to the information registration server, and instruction causing recording these pieces of related information into a mask recording means as a mask table;

the program being configured for transmitting the mask table after modification from the terminal to the information registration server via a network, when the transmission-permitting mask information or the transmission-prohibiting mask information corresponding to a certain field is modified;

the program being configured for recording, when the information registration server receives the mask table, into recording means a mask table before the reception of the mask table as an old mask table and recording into the recording means the received mask table as a new mask table; and the program being configured for comparing the old mask table and the new mask table; if there is a field having been changed from a field corresponding to the transmission-prohibiting mask information into a field corresponding to the transmission-permitting mask information, for transmitting information corresponding to this changed field from the terminal to the information registration server so as to record it on a second database within the information registration server; and, if there is a field having been changed from a field corresponding to the transmission-permitting mask information into a field corresponding to the transmission-prohibiting mask information, for deleting information corresponding to this changed field from the second database.

* * * * *